US007569665B2

(12) United States Patent
Bateman et al.

(10) Patent No.: US 7,569,665 B2
(45) Date of Patent: Aug. 4, 2009

(54) MOLECULAR MARKER

(75) Inventors: John Francis Bateman, Wattle Park (AU); David James Fitzgerald, Riddells Creek (AU)

(73) Assignee: Murdoch Childrens Research Institute Royal Children's Hospital, Victoria (AU)

( * ) Notice: Subject to any disclaimer, the term of this patent is extended or adjusted under 35 U.S.C. 154(b) by 0 days.

(21) Appl. No.: 10/699,035

(22) Filed: Oct. 31, 2003

(65) Prior Publication Data

US 2004/0214349 A1 Oct. 28, 2004

Related U.S. Application Data

(63) Continuation of application No. PCT/AU02/00542, filed on May 2, 2002.

(30) Foreign Application Priority Data

May 2, 2001 (AU) ..................................... PR4701

(51) Int. Cl.
*C07K 14/00* (2006.01)
(52) U.S. Cl. ...................... 530/350; 530/381
(58) Field of Classification Search ........................ None
See application file for complete search history.

(56) References Cited

U.S. PATENT DOCUMENTS

| 4,016,043 | A | 4/1977 | Schuurs et al. ................. 435/5 |
| 4,018,653 | A | 4/1977 | Mennen ....................... 600/572 |
| 4,424,279 | A | 1/1984 | Bohn et al. .................. 436/534 |
| 7,129,338 | B1 * | 10/2006 | Ota et al. .................... 536/23.5 |
| 7,368,531 | B2 * | 5/2008 | Rosen et al. ................. 530/350 |
| 2006/0003323 | A1 * | 1/2006 | Alsobrook et al. ............. 435/6 |

FOREIGN PATENT DOCUMENTS

| EP | 1067182 | 1/2001 |
| WO | 9853071 | 11/1998 |
| WO | 0058473 | 10/2000 |
| WO | 0118022 | 3/2001 |
| WO | 0142285 | 6/2001 |

OTHER PUBLICATIONS

Attwood TK. Genomics. The Babel of bioinformatics. Science. 290(5491):471-473, 2000.*
Skolnick et al. From genes to protein structure and function: novel applications of computational approaches in the genomic era. Trends Biotechnol. 18(1):34-9, 2000.*
Bork Powers and pitfalls in sequence analysis: the 70% hurdle. Genome Res. Apr. 2000;10(4):398-400.*
Doerks et al. Protein annotation: detective work for function prediction. Trends Genet. Jun. 1998;14(6):248-50.*
Arikawa-Hirasawa et al., Dyssegmental dysplasia, Silverman-Handmaker type, is caused by functional null mutations of the perlecan gene. *Nat. Genet.* Apr. 2001;27(4):431-4.
Arikawa-Hirasawa et al., "Perlecan is essential for cartilage and cephalic development," Nat Genet. Nov. 1999;23(3):354-8.
GenPept Database Acc. No. AAH 26919, submitted Apr. 4, 2002.
Fitzgerald et al., (2001) "A new FACIT of the collagen family: COL21A1", FEBS Letters 505:275-280.
Koch et al. (2001) "α1(XX) collagen, a new member of the collagen subfamily, fibril-associated collagens with interrupted triple helices", J. Biol. Chem. 276: 23120-23126.
Dgene Database Acc. No. AAB 88340, entered May 23, 2001.
GenPept Database Acc. No. AAK 38350, submitted Apr. 11, 2001.
GenPept Database Acc. No. AAB 42581, entered Feb. 8, 2001.
Fitzgerald et al. (2001) "The N-terminal N5 subdomain of the α3(VI) chain is important for collagen VI microfibril formation", J. Biol. Chem. 276: 187-193.
Gilges et al. (2000) "Polydom: a secreted protein with pentraxin, complement control protein, epidermal growth factor and von Willebrand factor A domains", Biochem J. 352: 49-59.
Chen et al. (1999) "Assembly of a novel cartilage matrix protein filamentous network: molecular basis of a differential requirement of von Willebrand factor a domains", Mol. Biol. Cell 10: 2149-2162.
Deák et al. (1999) "The matrilins: a novel family of oligomeric extracellular matrix proteins", Matrix Biology 18: 55-64.
GenPept Database Acc. No. AI 115125, entered Sep. 2, 1998.
GenBank Acc. No. NP 038620, published in 1998.
Emsley et al. (1998) "Crystal structure of the von Willebrand factor A1 domain and implications for the binding of platelet glycoprotein Ib", J. Biol. Chem. 273: 10396-10401.
Emsley et al. (1997) "Crystal structure of the I domain from integrin α2β1", J. Biol. Chem. 272: 28512-28517.

(Continued)

*Primary Examiner*—Maher M Haddad
(74) *Attorney, Agent, or Firm*—Baker Botts L.L.P.

(57) ABSTRACT

The present invention relates generally to a molecular marker of the integrity of the extracellular matrix in an animal including a human subject. More particularly, the present invention provides a molecular marker of cartilage integrity. The identification of the molecular marker in circulatory or tissue fluid is indicative of disrepair of the extracellular matrix and in particular cartilage such as caused or facilitated by trauma or a degenerative disease or other condition, for example, arthritis or autoimmunity. The molecular marker is preferably in the form of a glycoprotein but the instant invention extends to genetic sequences encoding the polypeptide portion of the glycoprotein. Expression analysis of such genetic sequences provides predictive utility in detecting normal or abnormal extracellular matrix development. The identification of the molecular marker of the present invention enables the development of a range of diagnostic and therapeutic agents for degeneration of extracellular matrix or the poor development of the matrix at the fetal and postnatal stages including testing for mutations in the gene sequence in human disease such as but not limited to cartilage disease or arthritis. In a most preferred embodiment, the molecular marker is referred to herein as "WARP" for von Willebrand Factor A-Related Protein. The corresponding genetic form of WARP is referred to herein as "WARP".

1 Claim, 9 Drawing Sheets

OTHER PUBLICATIONS

Kuo et al. (1997) "Type VI collagen anchors endothelial basement membranes by interacting with type IV collagen", J. Biol. Chem. 272: 26522-26529.

Beinkowska et al. (1997) "The von Willebrand factor A3 domain does not contain a metal ion-dependent adhesion site motif", J. Biol. Chem. 272: 25162-25167.

Zaverio M. Ruggeri (1997) "Perspectives series: cell adhesion in vascular biology", J. Clin. Invest., 99: 559-564.

Robertson et al., (1997) "Mapping and characterization of a novel cochlear gene in human and in mouse: a positional candidate gene for a deafness disorder, DFNA9", Genomics 46: 345-354.

GenBank Acc. No. O 42163, submitted in Jul. 1997.

GenBank Acc. No. NP 058042, published in 1997.

GenBank Acc. No. NP 034900, published in 1997.

Beck et al. (1996) "The C-terminal domain of cartilage matrix protein assembles into a triple-stranded α-helical coiled-coil structure", J. Mol. Biol. 256: 909-923.

Chan et al. (1996) "Site-directed mutagenesis of human type X collagen", J. Biol. Chem. 271: 13566-13572.

Tuckwell et al. (1996) "The A-domain of integrin α2 binds specifically to a range of collagens but is not a general receptor for the collagenous motif", Eur. J. Biochem. 241: 732-739.

GenBank Acc. No. NP 034899, published in 1996.

GenBank Acc. No. 1589549, published in 1996.

GenBank Acc. No. P11276, submitted Dec. 1995.

Qu et al. (1995) "Crystal structure of the I-domain from the CD11a/CD18 (LFA-1, $\alpha_L\beta 2$) integrin", Proc. Natl. Acad. Sci. USA 92: 10277-10281.

Haudenschild et al. (1995) "The role of coiled-coil α-helices and disulfide bonds in the assembly and stabilization of cartilage matrix protein subunits", J. Biol. Chem. 270: 23150-23154.

Lee et al. (1995) "Crystal structure of the domain from the α subunit of integrin CR3 (CDb/CD18)", Cell 80: 631-638.

Hansen et al. (1995) "Prediction of O-glycosylation of mammalian proteins: specificity patterns of UDP-GalNAc: polypeptide N-acetylgalactosaminyltransferase", Biochem. J. 308: 801-813.

Chan et al. (1995) "The three heavy-chain precursors for the inter-α-inhibitor family in mouse: new members of the multicopper oxidase protein group with differential transcription in liver and brain", Biochem. J. 306: 505-512.

Lefebvre et al. (1995) "Type X collagen gene expression in mouse chondrocytes immortalized by a temperature-sensitive simian virus 40 large tumor antigen", J. Cell Biol. 128: 239-245.

Engel et al. (1994) "Domain organizations of extracellular matrix proteins and their evolution", Development Supplement: 35-42.

Thompson et al. (1994) "Clustal W: improving the sensitivity of progressive multiple sequence alignment through sequence weighting, position-specific gap penalties and weight matrix choice", Nucleic Acids Res. 22: 4673-4680.

McMahon et al. (1994) "$C_2C_{12}$ cells: biophysical, biochemical, and immunocytochemical properties", Am. J. Physiol. 266: 1795-1802.

Denis et al. (1993) "Localization of von Willebrand factor binding domains to endothelial extracellular matrix and to type VI collagen", Arterioscler. Thromb. 13: 398-406.

Chan et al. (1993) "Characterization of an arginine 789 to cysteine substitution in α1(II) collagen chains of a patient with spondyloepiphyseal dysplasia", J. Biol. Chem. 268: 15238-15245.

Colombatti et al. (1993) "Type A modules: interacting domains found in several non-fibrillar collagens and in other extracellular matrix proteins", Matrix 13: 297-306.

GenBank Acc. No. P 56199, published in 1993.

GenBank Acc. No. S 78476, submitted Jan. 1993.

Trueb et al. (1992) "Type XIV collagen is a variant of undulin", Eur. J. Biochem., 207: 549-557.

Specks et al. (1992) "Structure of recombinant N-terminal globule of type VI collagen α3 chain and its binding to heparin and hyaluronan", EMBO J. 11: 4281-4290.

Yamagata et al. (1991) "The complete primary structure of type XII collagen shows a chimeric molecule with reiterated fibronectin region of type IX collagen, and short collagenous domains with an Arg-Gly-Asp site", J. Cell. Biol. 115: 209-221.

Parente et al. (1991) "Human type VII collagen: cDNA cloning and chromosomal mapping of the gene", Proc. Natl. Acad. Sci. USA 88: 6931-6935.

Chu et al. (1990) "Mosaic structure of globular domains in the human type VI collagen α3 chain: similarity to von Willebrand factor, fibronectin, actin, salivary proteins and aprotinin type protease inhibitor", EMBO J. 9: 385-393.

GenBank Acc. No. NP 00204, published in 1990.

Chu et al. (1989) "Sequence analysis of α1(VI) and α2(VI) chains of human type VI collagen reveals internal triplication of globular domains similar to the A domains of von Willebrand factor and two α2(VI) chain variants that differ in the carboxy terminus", EMBO J. 8: 1939-1946.

Ellis et al. (1988) "Sequence and expression of mRNSs encoding the $\alpha_1$ and $\alpha_2$ subunits of a DHP-sensitive calcium channel", Science 241: 1661-1664.

GenBank Acc. No. NP 004361, published in 1987.

Sadler et al. (1985) "Cloning and characterization of two cDNAs coding for human von Willebrand factor", Proc. Natl. Acad. Sci. USA 82: 6394-6398.

Mole et al. (1984) "Complete primary structure for the zymogen of human complement factor B", J. Biol. Chem. 259: 3407-3412.

Bateman et al. (1984) "Abnormal type I metabolism by cultured fibroblasts in lethal perinatal osteogenesis imperfecta", Biochem. J. 217: 103-115.

Schneike et al. (1983) "Embryonic lethal mutation in mice induced by retrovirus insertion into the α1(I) collagen gene", Nature 304: 315-320.

Sudo et al. (1983) "In vitro differentiation and calcification in a new clonal osteogenic cell line derived from newborn mouse calvaria", J. Cell. Biol. 96: 191-198.

Paulsson et al. (1982) "Radioimmunoassay of the 148-kilodalton cartilage protein", Biochem. J. 207: 207-213.

GenBank Acc. No. NM 013556, published in 1982.

Bonner et al. (1974) "A film detection method for tritium-labelled proteins and nucleic acids in polyacrylamide gels", Eur. J. Biochem. 46: 83-88.

Marmur et al. (1962) "Determination of the base composition of deoxyribonucleic acid from its thermal denaturation temperature", J. Mol. Biol. 5: 109-118.

Allen et al. (2006) "WARP is a novel multimeric component of the chondryte pericellular matrix that interacts with perlecan", J. Biol. Chem. 281: 7341-7349.

* cited by examiner

```
tcgatcaagagcccgccactccaggcgcgatgctgttctggactgcgttcagcatggctttgagtctgcgg      71
                   M   L   F   W   T   A   F   S   M   A   L   S   L   R     14
ttggcattggcgcggagcagcatagagcgcggttccacagcatcagaccccagggggacctgttgttcctg     143
  L   A   L   A   A   R   S   S   I   E   R   G   S   T   A   S   D   P   Q   G   D   L   L   F   L    38
ttggacagctcagccagcgtgtcacactatgagttctcaagagttcgggaatttgtggggcagctggtgct     215
  L   D   S   S   A   S   V   S   H   Y   E   F   S   R   V   R   E   F   V   G   Q   L   V   A        62
acgatgtctttcggaccccggggctctgcgtgctagtctggtgcacgtgggcagccagcctcacacagagttt  287
  T   M   S   F   G   P   G   A   L   R   A   S   L   V   H   V   G   S   Q   P   H   T   E   F        86
actttgaccagtacagttcaggccaggctatacgggatgccatccgtgttgcaccccaacgtatgggtgat    359
  T   F   D   Q   Y   S   S   G   Q   A   I   R   D   A   I   R   V   A   P   Q   R   M   G   D       110
accaacacaggcctggcactggcttatgccaaagaacaattgtttgctgaggaagcaggtgcccggccaggg   431
  T   N   T   G   L   A   L   A   Y   A   K   E   Q   L   F   A   E   E   A   G   A   R   P   G       134
gttcccaaggtgctggtgtgggtgacagatggtggctccagcgacccgtgggcccccctatgcaggagctc   503
  V   P   K   V   L   V   W   V   T   D   G   G   S   S   D   P   V   G   P   P   M   Q   E   L       158
aaggacctgggtgtcaccatcttcattgtcagcactggccgaggcaacctgttggagctgttggcagctgcc   575
  K   D   L   G   V   T   I   F   I   V   S   T   G   R   G   N   L   L   E   L   L   A   A   A       182
tcggctcctgccgagaagcacctacactttgtggatgtggatgatcttcctatcattgcccgggagctgcgg  647
  S   A   P   A   E   K   H   L   H   F   V   D   V   D   D   L   P   I   I   A   R   E   L   R       206
ggctccataactgatgcgatgcagccacaacagcttcatgcctcggaggttctgtccagtggcttccgcctg   719
  G   S   I   T   D   A   M   Q   P   Q   Q   L   H   A   S   E   V   L   S   S   G   F   R   L       230
tcctggccgcccctgctgacagcggactctggttactacgtgctggaattggtacctagcggcaaactggca   791
  S   W   P   P   L   L   T   A   D   S   G   Y   Y   V   L   E   L   V   P   S   G   K   L   A       254
accacaagacgccaacagctgcccgggaatgctaccagctggacctggacagatctcgacccggacacagac   863
  T   T   R   R   Q   Q   L   P   G   N   A   T   S   W   T   W   T   D   L   D   P   D   T   D       278
tatgaagtatcactgctgcctgagtccaacgtgcacctcctgaggccgcagcacgtgcgagtacgcacactg   935
  Y   E   V   S   L   L   P   E   S   N   V   H   L   L   R   P   Q   H   V   R   V   R   T   L       302
caagaggaggccgggccagaacgcatcgtcatctcgcatgcgaggccgcgcagcctccgcgtaagctgggcc  1007
  Q   E   E   A   G   P   E   R   I   V   I   S   H   A   R   P   R   S   L   R   V   S   W   A       326
cccgcgcttggccccggactccgctctcggctaccatgtacagctcggacctctgcagggcgggtccctagag 1079
  P   A   L   G   P   D   S   A   L   G   Y   H   V   Q   L   G   P   L   Q   G   G   S   L   E       350
cgcgtggaggtgccagcaggccagaacagcactaccgtccagggcctgacgccctgcaccacttacctggtg 1151
  R   V   E   V   P   A   G   Q   N   S   T   T   V   Q   G   L   T   P  Ⓒ  T   T   Y   L   V       374
actgtgactgccgccttccgctccggccgccagagggcgctgtcggctaaggcctgtacggcctctggcgcg  1223
  T   V   T   A   A   F   R   S   G   R   Q   R   A   L   S   A   K   A  Ⓒ  T   A   S   G   A       398
cggaccccgtgctccgcagtccatgcggccggaggctggaccgcgggagccctgaactgcctgcctgctcgtc 1295
  R   T   R   A   P   Q   S   M   R   P   E   A   G   P   R   E   P   *                               415
caccccggggggccctcttccctagcccggagagagagacactgctgctcgtgggttttcttgtggatggagtc 1367
gggtggggagatgggatgccggtcctgcctttgaccagcgttaattcctttcgtcgtttccccactggtcat   1439
cgccgcccttgcctgacttccgggaaacccgggtagcctcacgcgcaatggcggtcctctccggttgccagt   1511
ggagttgagcacacggtggtccttgggcaactcttggcgaggggatggacagtgtctgaggtcaggttgagg   1583
acataagacccaggaaccgccttcaggagaggaggccacagagtttccaacctgtgccaaaggctgggccct   1655
ctggtggcagggactacgcatggctttgaggaggcgttcaggaccatccaggtcctgcctgggcctagaaag   1727
tgggtaggagaaagggaagagagactagtgtagacaggattcccgaaaacttcctcaaggaaaggaaagata   1799
gggaggtatgctgggaggctgatgatgtggcattggttttcatcaagatgtcctgccagcctagaggccggg   1871
atctgtcagggtcactgactctgccttcctgccaggacctgcactgggccctcgatcagtgccaaggatgc   1943
agtcttttcacaggaatgggacgagaccttggcatttagggcctcagggataggagagccgcactatgacag   2015
attctaagggagcctcctgctttagtgtagggagcaaggtgtcatgcaggtgggctacctcctgccatcacc   2087
attaccctggggcatctgacagatacctaagggtggtcaggaacaggtttcctctcaagtccctatgtaggc   2159
ctctcctctcctctcagaatcatttgccttatcccaagcttactccatctcttcccactaatgacccggac   2231
tctaacaacaatacagtcagacagacataaactgtgcctgcagtctcattaaaatgctgtattttcgtcaa   2303
aaaaaaaa                                                                   2311
```

Figure 1A

```
human  MLPWTA GLALSLRLALARSGAERG PPASAPRGDLMFLLDSSASVSHYEFSRVREFVGQL  60    [SEQ ID NO:20]
mouse  MLFWTAR SMALSLRLALARSSIERG STASDPQGDLLFLLDSSASVSHYEFSRVREFVGQL  60    [SEQ ID NO:21]
        *:  .:*******    *...:*************************** human  VAPLPLGTGALRASLVHVGSRPYTEFPFGQHSSGEAAQDAVRASAQRMGDTHTGLALVYA  120
mouse  VATMSFGPGALRASLVHVGSQPHTEFTFDQYSSGQAIRDAIRVAPQRMGDTNTGLALAYA  120
       **  . *.***********: *:***.*.*:**** *.*:* *:*******.*****.**

human  KEQLFAEASGARPGVPKVLVWVTDGGSSDPVGPPMQELKDLGVTVFIVSTGRGNFLELSA  180
mouse  KEQLFAEEAGARPGVPKVLVWVTDGGSSDPVGPPMQELKDLGVTIFIVSTGRGNLLELLA  180
       *****::********************************:****:* * human  AASAPAEKHLHFVDVDDLHIIVQELRGSILDAMRPQQLHATEITSSGFRLAWPPLLTADS  240
mouse  AASAPAEKHLHFVDVDDLPIIARELRGSITDAMQPQQLHASEVLSSGFRLSWPPLLTADS  240
       **************** :***** :**** *::****:****** human  GYYVLELVPSAQPGAARRQQLPGNATDWIWAGLDPDTDYDVALVPESNVRLLRPQILRVR  300
mouse  GYYVLELVPSGKLATTRRQQLPGNATSWTWTDLDPDTDYEVSLLPESNVHLLRPQHVRVR  300
       **********.: ::* ***********.*.* **********:*.:** ** human  TRPEEAGPERIVISHARPRSLRVSWAPALGSAAALGYHVQFGPLRGGEAQRVEVPAGRNC  360
mouse  TLQEEAGPERIVISHARPRSLRVSWAPALGPDSALGYHVQLGPLQGGSLERVEVPAGQNS  360
       *  ***************************..:******:***.**. :********:*.

human  TTLQGLAPGTAYLVTVTAAFRSGRESALSAKACTPDGPRP PRPVPRAPTPGTASREP  418
mouse  TTVQGLTPCTTYLVTVTAAFRSGRQRALSAKACTASGARTR ---APQSMRPEAGPREP  415
       **:***:* *:*************: *******. .**:  * :: * ..***:*****
```

Figure 1C

| | | |
|---|---|---|
| collagenXIV | IADIVILVDGSWSIGRFNFRLVRLFLENLVSAFN--VGSEKTRVGLAQYSGDPRIEWHLN 58 | [SEQ ID NO:22] |
| collagenVII | AADIVFLLDGSSSIGRSNFREVRSFLEGLVLPFSGAASAQGVRFATVQYSDDPRTEFGLD 60 | [SEQ ID NO:23] |
| collagenXII | KADIVFLTDASWSIGDDNFNKVVKFIFNTVGAFD-EVNPAGIQVSFVQYSDEVKSEFKLN 59 | [SEQ ID NO:24] |
| collag nVI | AADIVFLVDSSWSAGKDRFLLVQEFLSDVVESLA--VGDNDFHFALVRLNGNPHTEFLLN 58 | [SEQ ID NO:25] |
| matrilin-2 | RADLVFIIDSSRSVNTYDYAKVKEFILDILQFLD--IGPDVTRVGLLQYGSTVKNEFSLK 58 | [SEQ ID NO:26] |
| matrilin-4 | PLDLVFMIDSSRSVRPFEFETMRQFLVGLLRSLD--VGLNATRVGVIQYSSQVSVFPLG 56 | [SEQ ID NO:27] |
| matrilin-3 | PLDLVFIIDSSRSVRPLEFTKVKITFVSRIIDTLD--IGATDTRVAVVNYASTVKIEFQLN 58 | [SEQ ID NO:28] |
| matrilin-1 | PTDLVFVFVVDSSRSVRPVEFEKVKVFLSQVIESLD--VGPNATRVGLVNYASTVKPEFPLR 58 | [SEQ ID NO:29] |
| VLA | QLDIVIVLDGSNSIYP--WDSVTAFLNDLLKRMD--IGPKQTQVGIVQYGENVTHEFNLN 56 | [SEQ ID NO:30] |
| WARP | QGDLLFLLDSSASVSHYEFSRVREFVGQLVATMS--FGPGALRASLVHVGSQPHTEFTFD 58 | [SEQ ID NO:31] |
| cochlin | KADIAFLIDGSYNIGQRRFNLQKNFVGKVAVMLG--IGTEGPHVGVVQASEHPKIEFYLK 58 | [SEQ ID NO:32] |
| vwf | LLDLVFLLDGSSRLSEAEFEVLKAFVVDMMERLR--ISQKWVRVAVVEYHDGSHAYIGLK 58 | [SEQ ID NO:33] |
| | *: :: *:* . . : . : | |

| | |
|---|---|
| collagenXIV | AYGTKDAVLDAVRNLPYKGGN-TLTGLALTYILENSFKPEAG---ARPGVSKIGILITDG 114 |
| collagenVII | ALGSGGDVIRAIRELSYKGGN-TRTGAAILHVADHVFLPQL----ARPGVPKVCILITDG 115 |
| collagenXII | TYNDKALALGALQNIRYRGGN-TRTGKALTFIKEKVLTWESG---MRKNVRVLG-VVTDG 114 |
| collagenVI | TYHSKQEVLSHIANMSYIGGS-NQTGKGLEYVIHSHLTEASGSR-AADGVPQVIVVLTDG 116 |
| matrilin-2 | TFKRKSEVERAVKRMRHLSTG-TMTGLAIQYALNIAFSEAEGARPLRENVPRIIMIVTDG 117 |
| matrilin-4 | AFSRREDMERAIRAVVPLAQG-TMTGLAIQYAMNVAFSEAEGARPSEERVPRVLVIVTDG 115 |
| matrilin-3 | TYSDKQALKQAVARITPLSTG-TMSGLAIQTAMEBAFTVEAGARGPMSNIPKVAIIVTDG 117 |
| matrilin-1 | AHGSKASLLQAVRRIQPLSTG-TMTGLALQFAITKALSDAEGGRARSPDISKVVIVVTDG 117 |
| VLA | KYSSTEEVLVAAKKIVQRGRGRQTMTALGTDTARKEAFTEARGAR---RGVKKVMVIVTDG 113 |
| WARP | QYSSGQAIRDAIR-VAPQRMGDTNTGLALAYAKEQLFAEEAGAR---PGVPKVLVWVTDG 114 |
| cochlin | NFTAAKEVLFAIKELGFRGGN-SNTGKALKHAAQKFFSMENGAR---KGIPKLIVVFLDG 114 |
| vwf | DRKRPSELRRIASQVKYAGSQVASTSEVLKYTLFQIFSKIDRPE--ASRIALLLMASQEP 116 |
| | : : . : . : |

Figure 2A

| | | |
|---|---|---|
| collagenXIV | KSQD--DVIPPAKNLRDAGIELFAIGVKN-----------ADINELKEIASEPDS-THVYN 161 | [SEQ ID NO:22] |
| collagenVII | KSQD--LVDTAAQRLKGQGVKLFAVGIKN-----------ADPEELKRVASQPTS-DFFFF 162 | [SEQ ID NO:23] |
| collagenXII | RSQD--EVKKAAFVIQQSGFSVFVVGVAD-----------VDYNELANIASKPSE-RHVFI 161 | [SEQ ID NO:24] |
| collagenVI | QSED--GFALPSAELKSADVNFAVGVEG------------ADERALGEVASEPLLSMHVFN 164 | [SEQ ID NO:25] |
| matrilin-2 | RPQD--SVAEVAAKARNTGILIFAIGVG------------QVDLNTLKAIGSEPHK-DHVFL 164 | [SEQ ID NO:26] |
| matrilin-4 | RPQD--RVAEVAAQARARGIEIYAVGVQ------------RADVGSLRTMASPPLD-QHVFL 162 | [SEQ ID NO:27] |
| matrilin-3 | RPQD--QVNEVAARARASGIELYAVGVD------------RADMESLKMMASKPLE-EHVFY 164 | [SEQ ID NO:28] |
| matrilin-1 | RPQD--SVRDVSERARASGIELFAIGLG------------RVDKATLRQIASEPQD-EHVDY 164 | [SEQ ID NO:29] |
| VLA | ESHDNHRLKKVIQDCEDENIQRFSIAILGSYNRGNLSTEKFVEEIKSIASEPTE-KHFFN 172 | [SEQ ID NO:30] |
| WARP | GSSD--PVGPPMQELKDLGVTIFIVSTG------------RGNLLELLAAASAPAE-KHLHF 161 | [SEQ ID NO:31] |
| cochlin | WPSD--DLEEAGIVAREFGVNVFIVSSVA-----------KPTTEELGMVQDIGFIDKAVCR 163 | [SEQ ID NO:32] |
| vwf | QRMSR-NFVRYVQGLKKKVIVIPVGIGP------------HANLKQIRLIEKQAPE-NKAFV 165 | [SEQ ID NO:33] |
| | : . . : | |
| collagenXIV | VADFNFMNSIVEGLTRTVCSR 182 | |
| collagenVII | VNDFSILRTLLPLVSRRVCTT 183 | |
| collagenXII | VDDFESFEKIEDNLITFVCET 182 | |
| collagenVI | LENVTSLHGLVGNLVSCIHSS 185 | |
| matrilin-2 | VANFSQIESLTSVFQNKLCTV 185 | |
| matrilin-4 | VESF-DIQEFGLQFQGRLCGK 182 | |
| matrilin-3 | VETYGVIEKLSARFQETPCAL 185 | |
| matrilin-1 | VESYNVIEKLAKKFQEAFCVV 185 | |
| VLA | VSDELALVTIVKTLGERIFAL 193 | |
| WARP | VDVD-DLPIIARELRGSITDA 181 | |
| cochlin | NNGFFSYQMPSWFGTTKYVKP 184 | |
| vwf | LSSVDELEQQRDEIVSYLCDL 186 | |

Figure 2A (continued)

```
coll XII    F3-3   PRNLKVTDETTDSFKTTWTQAPG--RVLRYRIIKRPVAG-GESREVTTP-PNQRRTLEN   [SEQ ID NO:34]
fibronect   F3-12  PSQMQVIDVQDNSISVRWLPSTS--PVTGYRVTTPKNGLGPSKTKTAS-PDQTEMTIEG   [SEQ ID NO:35]
WARP        F3-2   PERIVISHARPRSLRVSWAPALGPDSALGYHVQLGPLQG-GSLERVEVP-AGQNSTIVQG   [SEQ ID NO:36]
β4 integrin F3-3   PTRLVFSALGPTSLRVSWQEPRCERPLQGYSVEVQLLNG-GELHRLNLPNPAQTSVVVED   [SEQ ID NO:37]
coll XIV    F3-5   PQHLEVDEASTDSFRVSNKPTSS--DTAFYRLAWIPLDG-GESEEVVLS-GDADSYVIEG   [SEQ ID NO:38]
t nascin-R  F3-7   PKDITISNVTKDSVMVSWSPPVA--SFDYYRVSYRPTQV-GRLDSSVVP-NTVTEFTITR   [SEQ ID NO:39]
WARP        F3-1   PQQLHASEVLSSGFRESWPLLT-ADSGYYVLELVPSGKLATTRRQQLP-GNATSWTWTt   [SEQ ID NO:40]

coll XII    F3-3   LIPDTKYEVSVIPEYFSGPGTPLTGNAAT
fibronect   F3-1   LQPTVEYVVSVYAQNRNGESQPLVQTAVT
WARP        F3-2   LTPCTTYLVEVTAAFRSGRQRALSAKACT
β4 integrin F3-3   LLPNHSYVFRVRAQSQEGWGREREGVLTI
coll XIV    F3-5   LLPNTEYEVSLLAVFDDETESEVVAVLGA
tenascin-R  F3-7   LNPATEYEFSENSVRGREESERICTLVHT
WARP        F3-1   LDEDTDYEVSLLPESNVHLLRPQHVRVRT
```

Figure 2B

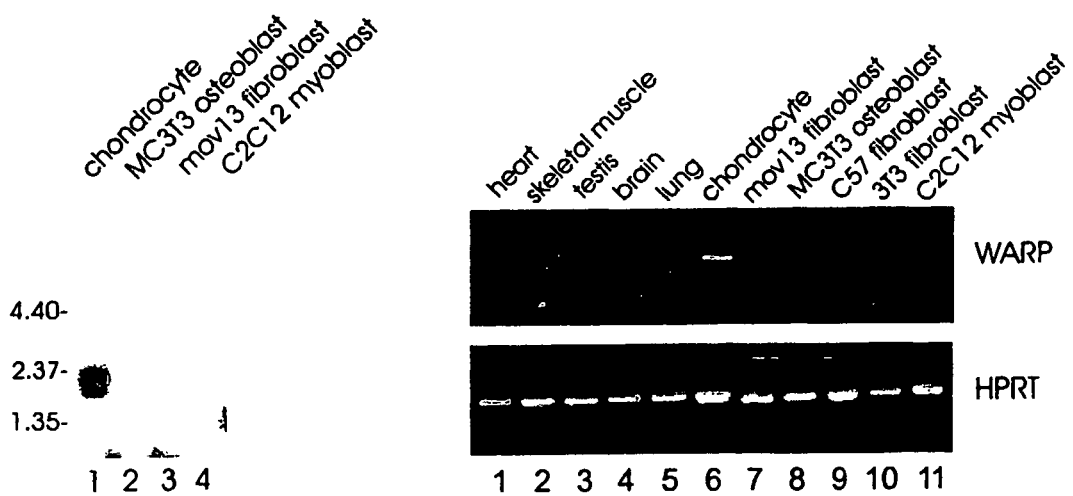
Figure 3A  Figure 3B
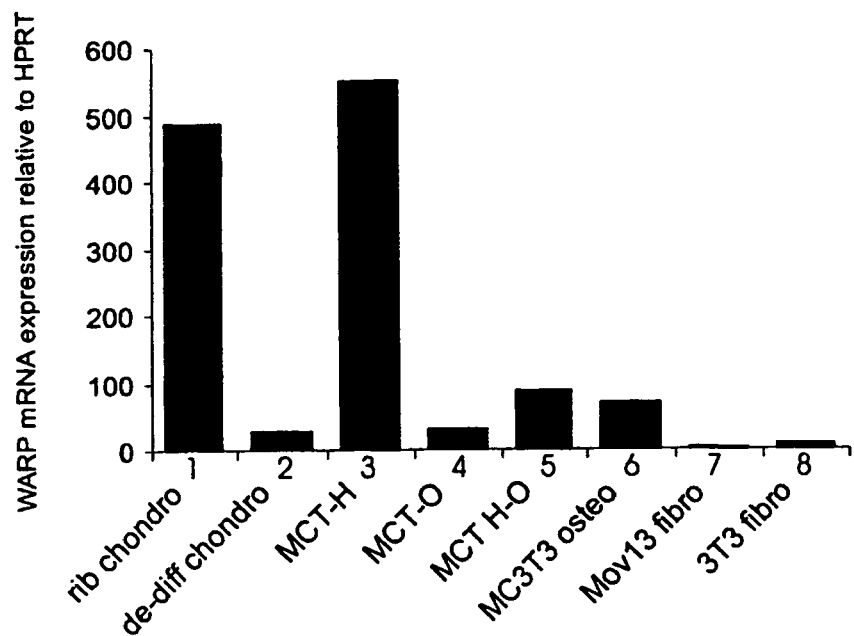
Figure 3C

MOLECULAR MARKER

The present invention is a continuation of International Application No. PCT/AU02/00542, filed May 2, 2002, published in English as International Publication No. WO02/088184 A1 on Nov. 7, 2002, which claims priority to Australian Application No. PR4701, filed May 2, 2001, all of which are incorporated herein by reference in their entireties.

SEQUENCE LISTING

The specification further incorporates by reference a substitute Sequence Listing submitted via EFS on Oct. 30, 2007. Pursuant to 37 C.F.R. §1.52(e)(5), the substitute Sequence Listing text file, identified as 718380142.txt, is 2.0 Mb and was created on Oct. 30, 2007. The substitute Sequence Listing, electronically filed herewith, does not extend beyond the scope of the specification and thus does not contain new matter.

FIELD OF THE INVENTION

The present invention relates generally to a molecular marker of the integrity of the extracellular matrix in an animal including a human subject. More particularly, the present invention provides a molecular marker of cartilage integrity. The identification of the molecular marker in circulatory or tissue fluid is indicative of disrepair of the extracellular matrix and in particular cartilage such as caused or facilitated by trauma or a degenerative disease or other condition, for example, arthritis or autoimmunity. The molecular marker may be in the form of a glycoprotein or genetic sequences encoding the polypeptide portion of the glycoprotein. Expression analysis of such genetic sequences provides predictive utility in detecting normal or abnormal extracellular matrix development. The identification of the molecular marker of the present invention enables the development of a range of diagnostic and therapeutic agents for degeneration of extracellular matrix or the poor development of the matrix at the fetal and postnatal stages, including testing for mutations in the gene sequence in human disease, such as, but not limited to, cartilage disease or arthritis. In a most preferred embodiment, the molecular marker is referred to herein as "WARP" for von Willebrand Factor A-Related Protein. The corresponding genetic form of WARP is referred to herein as "WARP".

BACKGROUND OF THE INVENTION

Reference to any prior art in this specification is not, and should not be taken as, an acknowledgment or any form of suggestion that this prior art forms part of the common general knowledge in any country.

The extracellular matrix (ECM) is a complex mixture of collagens, non-collagenous glycoproteins, and proteoglycans that interact to provide a structural scaffold, as well as specific cues for the maintenance, growth and differentiation of cells and tissues. The protein cores of a large number of ECM molecules are composed of different combinations of a finite collection of modules (Engel et al., Development Suppl. 35-42, 1994). The conservation of amino acid sequence of these modules between different ECM proteins and protein families provides us with the opportunity to identify new proteins by database homology searching to help reveal additional modular ECM proteins.

One module present in a number of proteins is the type A-domain, first described in von Willebrand factor (reviewed in Colombatti et al., Matrix 13: 297-306, 1993). Members of the expanding von Willebrand factor type A-domain (VA) protein superfamily participate in a variety of functions including hemostasis, cell adhesion and protein-protein interactions between matrix molecules. ECM components that contain one or more VA domains include collagens types VI (Chu et al., EMBO J. 9: 385-393, 1990; Chu et al., EMBO J. 8: 1939-1946, 1989), VII (Parente et al., Proc. Natl. Acad. Sci. USA 88: 6931-6935, 1991), XII (Yamagata et al., J. Cell Biol. 115: 209-221, 1991), XIV Trueb et al., Eur. J. BioChem. 207: 557, 1992), and XX (Koch et al., J. Biol. Chem. 276: 23120-23126, 2001), matrilins-1, -2, -3, -4 (reviewed in Deak et al., Matrix Biol. 18: 55-64, 1999), cochlin (Robertson et al., Genomics 46: 345-354, 1997), polydom (Gilges et al., BioChem. J. 352: 49-59, 2000) and nine transmembrane α integrin chains (α1, α2, α10, α11, αL, αM, αX, αD and αE) (reviewed in Lee et al., Cell 80: 631-638, 1995), where they are also known as an 'I' domain. Non-matrix proteins that contain VA domains include complement system proteins (C2, B) (Mole, J. E., J. Biol. Chem. 259: 3407-3412, 1984), inter-α-trypsin inhibitor (subunits H1-H3) (Chan et al., BioChem. J. 306: 505-512, 1995) α2β subunit of L-type voltage-dependent $Ca^{2+}$ channel (Ellis et al., Science 241: 1661-1664, 1988) in addition to the archetypal VA domains of von Willebrand factor itself (Sadler et al., Proc. Natl. Acad. Sci. USA 82: 6394-6398).

The crystal structure for several VA domains have been solved including the A1 (Emsley et al., J. Biol. Chem. 273: 10396-10401, 1998) and A3 Bienkowska et al., J. Biol. Chem. 272: 25162-25167, 1997) domains of vWF, and the I domain of integrins αM (Lee et al., 1995, supra), αL (Qu, A. and Leahy, D. J., Proc. Natl. Acad. Sci. USA 92: 10277-10281, 1995) and α2 (Emsley et al., J. Biol. Chem. 272: 28512-28517, 1997). These studies show that the VA module is an independently folding protein unit that attains a classic αβ 'Rossman' fold consisting of a parallel β sheet surrounded by amphipathic α helices, and in the majority of VA domains, a metal ion-dependent adhesion site (MIDAS) at the C-terminal end of the β sheet. The MIDAS motif, which consists of five conserved amino acids (DxSxS, T, D), act together with surrounding residues to bind divalent cations and gives I domains of integrins their adhesive and ligand binding properties (Lee et al., 1995, supra). However, not all VA domains contain this motif, for example, the A1 and A3 A-domains of von Willebrand Factor lack some of these conserved amino acids and are not predicted to bind metal ions (Emsley et al., 1998, supra; Bienkowska et al., 1997, supra) and the binding of collagen to the A3 domain is not metal ion dependent (Bienkowska et al., 1997, supra).

VA domains appear to play an important role in protein-protein interactions. In von Willebrand factor, they interact with subendothelial heparans, collagens I, III, (reviewed by Ruggeri, Z. M., J. Clin. Invest. 99: 559-564, 1997) and collagen VI (Denis et al., Arteriosclerosis & Thrombosis 13: 398-406, 1993); in integrins the I domain interacts with several collagens (Tuckwell et al., Eur. J. BioChem. 241: 732-739, 1996); and in collagen VI VA domains interact with heparin Specks et al., EMBO J. 11: 4281-4290, 1992) and collagen IV (Kuo et al., J. Biol. Chem. 272: 26522-26529, 1997). In ECM molecules, the ability of VA domains to interact with other proteins and with each other to promote higher-order structure formation may be crucial in providing a linkage between ECM structural networks. For example, in collagen VI, a specific N-terminal α3(VI) collagen VA domain (N5) is important for the assembly of collagen VI tetramers into functional microfibrils (Fitzgerald et al., J. Biol. Chem. 276: 187-193, 2001) and in matrilin-1, interchain assembly and microfilament formation is promoted by the interaction of the VA domains in adjacent matrilin molecules (Chen et al., Mol. Biol. Cell 10: 2149-2162, 1999).

As described herein, a new member of the VA-domain protein superfamily referred to herein as von Willebrand factor A Related-Protein or WARP has been identified. WARP provides, therefore, a molecular marker of the integrity of the ECM and in particular cartilage. WARP is a novel disulfide-bonded oligomeric ECM glycoprotein that is expressed in cartilage. A genetic sequence encoding WARP is represented herein in itallicized form, i.e., WARP. Both WARP and WARP represent molecular markers of ECM and in particular cartilage integrity. The presence or absence of WARP or altered levels of WARP relative to normal controls is proposed to be indicative of disease conditions such as arthritis or cartilage disease. Furthermore, mutations in WARP are proposed to be genetic indicators of a propensity for a disease condition to occur or provide a diagnostic basis for the presence of a disease condition.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1, <400>2, etc. A sequence listing is provided after the claims.

molecular marker of ECM, and in particular cartilage integrity, in the form of a new member of the von Willebrand factor A (VA) domain superfamily of extracellular matrix proteins, which is referred to herein as "WARP" for von Willebrand Factor A Related-Protein, has been identified. To identify novel VA-containing proteins, the EST database at NCBI was searched using the N8 VA-type domain protein sequence from the α3(VI) collagen chain. A series of overlapping EST clones with homology to N8 that represented a novel VA protein was identified. The full-length WARP cDNA, referred to herein as "WARP", is 2.3 kb in size and encodes a protein of 415 amino acids. The protein contains, from the N-terminus, a putative signal sequence, a single VA-like domain, two fibronectin type III-like repeats, and a short proline and arginine-rich segment. Northern blot and Real-time (RT)-PCR analysis indicates that WARP is expressed in rib chondrocytes. Further experiments demonstrated that WARP forms disulphide-bonded oligomers in vitro and in vivo. WARP, therefore, is a new member of VA domain superfamily of extracellular matrix proteins, which is expressed by chondrocytes and is capable of forming oligomers.

Accordingly, one aspect of the present invention provides an isolated polypeptide or a derivative or homolog thereof, which in situ forms part of the ECM in an animal, wherein the polypeptide comprises a VA-related domain encoded by a nucleotide sequence substantially as set forth in SEQ ID NO:1 or its complementary form or a nucleotide sequence having at least about 65% similarity thereto or a nucleotide sequence capable of hybridizing to SEQ ID NO:1 or its complementary form under low stringency conditions.

This polypeptide is WARP.

In one embodiment, the WARP forms part of the ECM in a mouse and comprises an amino acid sequence encoded by a nucleotide sequence substantially as set forth in SEQ ID NO: 3 or its complementary form or a nucleotide sequence having at least about 65% similarity thereto or a nucleotide sequence capable of hybridizing to SEQ ID NO: 3 or its complementary form under low stringency conditions.

In another embodiment, the WARP forms part of the ECM in a human and comprises an amino acid sequence encoded by a nucleotide sequence substantially as set forth in SEQ ID NO: 5 or its complementary form or a nucleotide sequence having at least about 65% similarity thereto or a nucleotide sequence capable of hybridizing to SEQ ID NO: 5 or its complementary form under low stringency conditions.

The amino acid sequences for the mouse and human WARP are set forth in SEQ ID NOs:4 and 6, respectively or have amino acid sequences having at least about 65% similarity to either SEQ ID NO:4 or SEQ ID NO:6.

The present invention further provides nucleic acid molecules such as those set forth in SEQ ID NO:1 or SEQ ID NO:3 or SEQ ID NO:5 which encode the WARP polypeptide of the present invention. The present invention extends to nucleotide sequences having at least about 65% similarity to SEQ ID NO:1 or SEQ ID NO:3 Or SEQ ID NO:5 or a nucleotide sequence capable of hybridizing to SEQ ID NO:1 or SEQ ID NO:3 or SEQ ID NO:5 or their complementary form under low stringency conditions.

Another aspect of the present invention provides a method for producing a recombinant WARP by introducing a nucleic acid molecule comprising the nucleotide sequence set forth in SEQ ID NO:3 or SEQ ID NO:5 or their complementary forms or a nucleotide sequence having at least about 65% similarity to SEQ ID NO:3 or SEQ ID NO:5 or their complementary forms or a nucleotide sequence capable of hybridizing to SEQ ID NO:3 or SEQ ID NO:5 or their complementary forms under low stringency conditions into a cell, culturing the cell or population of cells under conditions sufficient to permit expression of said nucleic acid molecule and then recovering the recombinant polypeptide.

The present invention extends to a method of identifying a nucleotide sequence likely to encode a WARP by interrogating an animal genome database conceptually translated into different reading frames with an amino acid sequence defining a VA domain and identifying a nucleotide sequence corresponding to a sequence encoding the VA domain.

Furthermore, the present invention contemplates a method of detecting a loss of ECM integrity in an animal subject by screening body fluid from the animal for the presence of a WARP or fragment thereof wherein the presence of the WARP or fragment is indicative of a loss of ECM integrity.

Still another aspect of the present invention provides a cartilage-specific promoter or functional derivative or homolog thereof which in situ is operably linked to a nucleotide sequence comprising SEQ ID NO:3 or SEQ ID NO:5 or their complementary forms or a nucleotide sequence having at least about 65% similarity to SEQ ID NO:3 or SEQ ID NO:5 or their complementary forms or a nucleotide sequence capable of hybridizing to SEQ ID NO:3 or SEQ ID NO:5 or their complementary forms under low stringency conditions.

The identification of WARP permits the detection of mutations in WARP such as those involved in disease conditions such as cartilage disease or arthritis or in a propensity for the development of disease conditions. WARP expression may also be a sensitive indicator of cartilage cell differentiation and is proposed to be useful in monitoring repair, regeneration or other disease processes in a subject. Furthermore, WARP may be used to condition or stabilize stem cells in order to facilitate imprinting of stem cells for tissue replacement therapy.

Genetically modified animals such as transgenic "knock-in" animals or "knock-out" animals are also contemplated by the present invention. Such animals, e.g. mice or rabbits or other laboratory test animals may be useful in the generation of disease models where there is under- or over-expression of WARP.

BRIEF DESCRIPTION OF THE FIGURES

FIG. 2 is a representation of the alignment of VA domain and F3 repeats of WARP with homologous domains in other ECM proteins. Alignments were performed using CLUSTALW (Thompson et al., 1994, supra). (A) Alignment of VA domains from several ECM and non-ECM proteins. Sequences are matrilin-2 (SEQ ID NO:26) (GenBank Accession #NP_058042, amino acids 55-239), matrilin-4 (SEQ ID NO:27) (NP_038620, 34-218), matrilin-3 (SEQ ID NO:28) (NP_034900 76-260), matrilin-1 (SEQ ID NO:29) (NP_034899, 43-227), collagen XIV (SEQ ID NO:22) (S78476, 156-337), collagen XII (SEQ ID NO:24) (NP_004361, 2321-2503), collagen VII (SEQ ID NO:23), collagen VI (SEQ ID NO:25), WARP (SEQ ID NO:31) (32-212), cochlin (SEQ ID NO:32) (O42163, 160-142), VLA-1α-integrin (SEQ ID NO:30) (P56199, 142-334) and vwf (SEQ ID NO:33) (von Willebrand factor). Sites where amino acids are identical in all sequences are marked with an asterisk, conserved substitutions are marked with a colon and semi-conserved substitutions with a full-stop. (B) Alignment of F3 repeats from a sample of ECM proteins. Sequences are WARP F3 domain 2 (SEQ ID NO:36) (308-394), collagen XIV (SEQ ID NO:38) (S78476, 627-711), β34 integrin chain (SEQ ID NO:37) (NP_000204, 1461-1548), collagen XII SEQ ID NO:34) (NP_004361, 726-810), fibronectin (SEQ ID NO:35) (P11276, 1635-1720), WARP F3 domain 1 (SEQ ID NO:40) (215-301) and tenascin R (SEQ ID NO:39) (1589549, 867-951). Alignments are shaded using BOX-SHADE. Identical positions are shown within dark boxes and conserved substitutions in grey boxes.

FIG. 3 is a photographic representation showing expression of WARP mRNA in mouse tissues and cell lines. (A) Northern blot analysis of WARP. Poly(A) mRNA isolated from primary mouse chondrocytes (lane 1), MC3T3 osteoblasts (lane 2), Mov13 fibroblasts (lane 3) and C2C12 myoblasts (lane 4) was fractionated on a 1% v/v agarose gel and transferred to nylon membrane. The membrane was probed with [32P]dCTP-labeled WARP cDNA fragment and exposed to X-ray film. The migration position of RNA markers in kb is indicated on left. (B) RT-PCR analysis of WARP mRNA expression. Total RNA was isolated from mouse tissues (lanes 1-6) and cell lines (lanes 7-11), treated with DNase to remove contaminating genomic DNA, and added to an oligo d(T)-primed RT reaction followed by PCR using primers specific for WARP (upper panel) and HPRT (lower panel). (C) Real-time PCR analysis of WARP mRNA expression. Each reaction contained oligo d(T)-primed cDNA, primers and fluorescently-labeled probes specific for WARP and HPRT. Data are represented as WARP signal relative to HPRT signal. The cDNA templates used were: 1, primary rib chondrocytes; 2, de-differentiated chondrocytes; 3, MCT cells induced to a hypertrophic chondrocyte-like phenotype; 4, MCT cells induced to an osteoblast-like phenotype; 5, MCT chondrocytes induced to change from hypertrophic chondrocyte-like to osteoblast-like phenotype; 6, MC3T3 osteoblasts; 7, Mov13 fibroblasts; and 8, 3T3 fibroblasts.

Figure 1B:
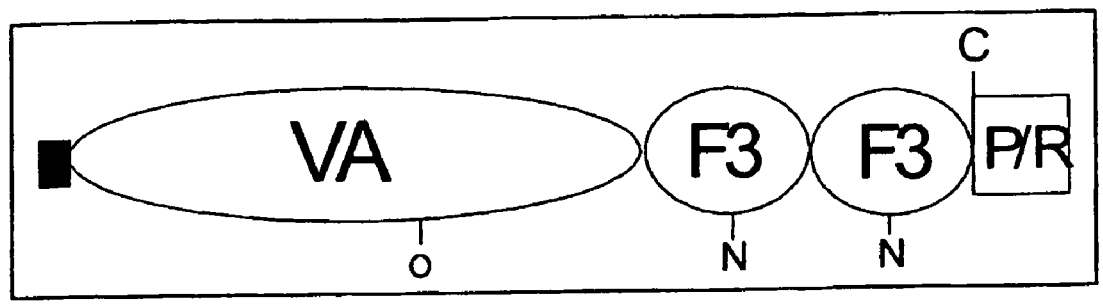
FIG. 1 is a representation of the structure and modular organization of WARP. (A) Nucleotide (SEQ ID NO: 41) and deduced amino acid sequence (SEQ ID NO: 21) of WARP. The stop codon at nucleotides 1275-1277 is marked with an asterix and a potential polyadenylation site at nucleotides 2279-2285 is shown in bold type. The position of potential N-linked ($Asn^{264}$ and $Asn^{359}$) and O-linked ($Ser^{148}$, $Thr^{361}$ and $Thr^{400}$) glycosylation sites are underlined. C-terminal cysteine residues ($Cys^{369}$ and $Cys^{393}$) available for disulfide bond formation are circled. (B) The modular structure of WARP is shown using standard symbols to represent conserved ECM protein modules (Bork, P. and Bairoch, A., TIBS 20 poster C02, 1995). VA, VA-domain; F3, fibronectin type III domain; P/R. proline/arginine-rich segment. Approximate positions of N- and O-linked glycosylation sites and Cys residues, conserved in both mouse and human sequences, are indicated. (C) Alignment of the amino acid sequences of the human (SEQ ID NO:20) and mouse (SEQ ID NO:21) WARP protein sequences. The predicted N-terminal signal sequence is boxed and the position of potential N-linked ($Asn^{264}$ and $Asn^{359}$) and O-linked ($Ser^{148}$ and $Thr^{361}$) glycosylation sites conserved in both sequences are underlined. The conserved C-terminal cysteine residue ($Cys^{393}$) available for disulfide bond formation is boxed. Alignments were performed using CLUSTALW (Thompson et al, Nucl. Acids Res. 22 4673-4680, 1994). Sites where amino acids are identical in both sequences are marked with an asterisk, conserved substitutions are marked with a colon and semi-conserved substitutions with a full-stop.

A summary of sequence identifiers is provided below:

| SUMMARY OF SEQUENCE IDENTIFIERS | |
|---|---|
| SEQ ID NO: | DESCRIPTION |
| 1 | Nucleotide sequence of human VA domain |
| 2 | Amino acid sequence of human VA domain |
| 3 | Nucleotide sequence of mouse WARP |
| 4 | Amino acid sequence of mouse WARP |
| 5 | Nucleotide sequence of human WARP |
| 6 | Amino acid sequence of human WARP |
| 7 | Nucleotide sequence of mouse VA domain |
| 8 | Amino acid sequence of human VA domain |
| 9 | NR1 primer |
| 10 | NF4 primer |
| 11 | mHPRT1 primer |

-continued

SUMMARY OF SEQUENCE IDENTIFIERS

| SEQ ID NO: | DESCRIPTION |
|---|---|
| 12 | mHPRT2 primer |
| 13 | WARP probe |
| 14 | WARP primer |
| 15 | WARP primer |
| 16 | HPRT probe |
| 17 | HPRT primer |
| 18 | HPRT primer |
| 19 | genomic sequence of human WARP |
| 20 | Alignment of the amino acid sequences of the human and WARP protein sequence |
| 21 | Alignment of the amino acid sequence of the murine WARP protein sequence |
| 22 | collagen XIV [FIG. 2A] |
| 23 | collagen VII [FIG. 2A] |
| 24 | collagen XII [FIG. 2A] |
| 25 | collagen VI [FIG. 2A] |
| 26 | matrilin-2 [FIG. 2A] |
| 27 | matrilin-4 [FIG. 2A] |
| 28 | matrilin-3 [FIG. 2A] |
| 29 | matrilin-1 [FIG. 2A] |
| 30 | VLA [FIG. 2A] |
| 31 | WARP [FIG. 2A] |
| 32 | cochlin [FIG. 2A] |
| 33 | vwf [FIG. 2A] |
| 34 | coll XII F3-3 [FIG. 2B] |
| 35 | fibronect F3-12 [FIG. 2B] |
| 36 | WARP F3-2 [FIG. 2B] |
| 37 | β4 integrin F3-3 [FIG. 2B] |
| 38 | coll XIV F3-5 [FIG. 2B] |
| 39 | tenascin-R F3-7 [FIG. 2B] |
| 40 | WARP F3-1 [FIG. 2B] |
| 41 | WARP [FIG. 1A] |

A summary of the abbreviations used is provided below:

ABBREVIATIONS

| ABBREVIATION | DESCRIPTION |
|---|---|
| ECM | extracellular matrix |
| WARP | von Willebrand Factor A domain related-protein |
| WARP | genetic sequence encoding WARP |
| VA | von Willebrand Factor A domain |
| N-terminus | amino-terminus |
| C-terminus | carboxyl-terminus |
| EST | expressed sequence tag |
| FACIT | Fibril-Associated Collagens with Interrupted Triple-Helices |
| PCR | polymerase chain reaction |
| bp | base pairs |
| kDa | kilodalton |
| SDS | sodium dodecyl sulfate |
| DTT | dithiothreitol |

DETAILED DESCRIPTION OF THE INVENTION

The present invention is predicated in part on the identification of a new member of the von Willebrand Factor A (VA) domain superfamily of extracellular matrix (ECM) proteins and to a genetic sequence encoding same. The novel polypeptide of the present invention and its encoding genetic sequence as well as derivatives, homologs and analogs thereof are useful as molecular markers of the integrity of the ECM and in particular cartilage and as indicators of disease, trauma or poor development in animal including human subjects. The instant polypeptide is referred to herein as "WARP" for von Willebrand Factor A-Related-Protein.

Accordingly, one aspect of the present invention provides an isolated polypeptide or a derivative or homolog thereof which in situ forms part of the ECM in an animal wherein said polypeptide comprises a VA-related domain encoded by a nucleotide sequence substantially as set forth in SEQ ID NO:1 or its complementary form or a nucleotide sequence having at least about 65% similarity thereto or a nucleotide sequence capable of hybridizing to SEQ ID NO:1 or its complementary form under low stringency conditions.

The nucleotide sequence set forth in SEQ ID NO:1 represents the nucleotide sequence of the human VA domain. An example of a homolog of this sequence from a murine source is set forth in SEQ ID NO:7.

Reference herein to a "polypeptide" or a "WARP" or a protein form of a molecular marker includes a protein in a monomeric or oligomeric state and/or in a folded or unfolded state as well as a polypeptide associated with non-proteinaceous moieties such as carbohydrates, lipids or phosphate groups. Most preferably, the polypeptide is a glycoprotein. The term "glycoprotein" means a polypeptide associated with carbohydrate moieties, as well as a glycosylated polypeptide. It is not the intention of the present invention to be limited solely to a glycoprotein since the polypeptide portion may have utility on its own such as its ability to induce antibody formation, in diagnostic assays and for therapeutic applications.

The present invention further contemplates the WARP polynucleotide in crystalline form where the crystal structure has been solved. Such a solved structure is useful for rational design of antagonists and agonist of the molecule as well as homologs of the molecules.

Reference herein to an "animal" includes any vertebrate animal comprising an ECM and in particular cartilage and includes humans, primates, livestock animals (e.g. sheep, goats, cows, pigs, horses, donkeys), companion animals (e.g. dogs, cats), laboratory test animals (e.g. mice, rats, rabbits, guinea pigs) and captured wild animals.

In one particularly preferred embodiment, the subject WARP is of murine origin and in particular mouse origin and comprises an amino acid sequence encoded by a nucleotide sequence substantially as set forth in SEQ ID NO:3.

Accordingly, another aspect of the present invention provides an isolated polypeptide or a derivative or homolog thereof which in situ forms part of the ECM in a mouse wherein said polypeptide comprises an amino acid sequence encoded by a nucleotide sequence substantially as set forth in SEQ ID NO:3 or its complementary form or a nucleotide sequence having at least about 65% similarity thereto or a nucleotide sequence capable of hybridizing to SEQ ID NO:3 or its complementary form under low stringency conditions.

In another embodiment, the instant polypeptide is of human origin and is encoded by a nucleic acid molecule substantially as set forth in SEQ ID NO:5. Such a polypeptide is referred to herein as human WARP.

According to this embodiment, there is provided an isolated polypeptide or a derivative or homolog thereof which in situ forms part of the ECM in a human wherein said polypeptide comprises an amino acid sequence encoded by a nucleotide sequence substantially as set forth in SEQ ID NO:5 or its complementary form or a nucleotide sequence having at least about 65% similarity thereto or a nucleotide sequence capable of hybridizing to SEQ ID NO:5 or its complementary form under low stringency conditions.

The term "similarity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In a particularly preferred embodiment, nucleotide and sequence comparisons are made at the level of identity rather than similarity.

Terms used to describe sequence relationships between two or more polynucleotides or polypeptides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as, for example, disclosed by Altschul et al. (Nucl. Acids Res. 25: 3389, 1997). A detailed discussion of sequence analysis can be found in Unit 19.3 of Ausubel et al. ("*Current Protocols in Molecular Biology*", John Wiley & Sons Inc., 1994-1998, Chapter 15).

The terms "sequence similarity" and "sequence identity" as used herein refers to the extent that sequences are identical or functionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

Preferably, the percentage (%) similarity or identity is at least about 70%, more preferably at least about 75%, still more preferably at least about 80%, even more preferably at least about 85%, yet even more preferably at least about 90-100% such as 91% or 92% or 93% or 94% or 95% or 96% or 97% or 98% or 99%.

Reference herein to a low stringency includes and encompasses from at least about 0 to at least about 15% v/v formamide and from at least about 1 M to at least about 2 M salt for hybridization, and at least about 1 M to at least about 2 M salt for washing conditions. Generally, low stringency is at from about 25-30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $Tm=69.3+0.41$ (G+C)% (Bonner and Laskey, Eur. J. BioChem. 46: 83, 1974). However, the Tm of a duplex DNA decreases by 1° C. with every increase of 1% in the number of mismatch base pairs (Marmur and Doty, J. Mol. Biol. 5: 109, 1962). Formamide is optional in these hybridization conditions. Accordingly, particularly preferred levels of stringency are defined as follows: low stringency is 6× SSC buffer, 0.1% w/v SDS at 25-42° C.; a moderate stringency is 2× SSC buffer, 0.1% w/v SDS at a temperature in the range 20° C. to 65° C.; high stringency is 0.1× SSC buffer, 0.1% w/v SDS at a temperature of at least 65° C.

In a particularly preferred embodiment, the present invention is directed to an isolated polypeptide of human origin comprising a sequence of amino acids defining a VA-related domain and having an amino acid sequence substantially as set forth in SEQ ID NO:2 or an amino acid sequence having at least about 65% similarity thereto. A homolog of murine origin comprises a VA-related domain having the amino acid sequence set forth in SEQ ID NO:8.

Even more particularly, another aspect of the present invention contemplates an isolated polypeptide or a derivative or homolog thereof which in situ forms part of the ECM in a mouse, said polypeptide comprising the amino acid sequence substantially as set forth in SE ID NO:4 or an amino acid sequence having at least about 65% similarity thereto.

In another embodiment, the present invention provides an isolated polypeptide or a derivative or homolog thereof which in situ forms part of the ECM in a human, said polypeptide comprising the amino acid sequence substantially as set forth in SE ID NO:6 or an amino acid sequence having at least about 65% similarity thereto.

As stated above, the polypeptide of the present invention is also referred to as "WARP" meaning a von Willebrand Factor A Related-Protein. Reference herein to a subject polypeptide or WARP includes reference to a derivative, homolog or analog thereof. The instant polypeptide or WARP is also referred to as a molecular marker.

A "derivative" includes a mutant, fragment, part, portion or hybrid molecule. A derivative generally but not exclusively carries a single or multiple amino acid substitution, addition and/or deletion.

A "homolog" includes an analogous polypeptide having at least about 65% similar amino acid sequence from another animal species or from a different locus within the same species.

Generally, the term "analogous polypeptide" means that the polypeptide or WARP is performing the same function or is part of the same structure between or within animal species. However, the present invention extends to any ECM protein including polypeptide having an amino acid sequence substantially at least about 65% similar to SEQ ID NO:4 or SEQ ID NO:6.

An "analog" is generally a chemical analog. Chemical analogs of the subject polypeptide contemplated herein include, but are not limited to, modification to side chains, incorporation of unnatural amino acids and/or their derivatives during peptide, polypeptide or protein synthesis and the use of crosslinkers and other methods which impose conformational constraints on the proteinaceous molecule or their analogs.

Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitization, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 1.

TABLE 1

| Non-conventional amino acid | Code |
| --- | --- |
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |

TABLE 1-continued

| Non-conventional amino acid | Code |
|---|---|
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl)carbamylmethyl)glycine | Nnbhm |
| 1-carboxy-1-(2,2-diphenyl-ethylamino)cyclopropane | Nmbc |
| L-N-methylalaninse | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-Nmethylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcylcopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |

TABLE 1-continued

| Non-conventional amino acid | Code |
|---|---|
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl)carbamylmethyl)glycine | Nnbhe |

Crosslinkers can be used, for example, to stabilize 3D conformations, using homo-bifunctional crosslinkers such as the bifunctional imido esters having $(CH_2)n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogs by introducing covalent bonds such as forming an amide bond between the N and C termini, between two side chains or between a side chain and the N or C terminus.

The present invention further contemplates chemical analogs of the subject polypeptide capable of acting as antagonists or agonists of the WARP or which can act as functional analogs of the WARP. Chemical analogs may not necessarily be derived from the instant polypeptide but may share certain conformational similarities. Alternatively, chemical analogs may be specifically designed to mimic certain physiochemical properties of the subject polypeptide. Chemical analogs may be chemically synthesized or may be detected following, for example, natural product screening. The latter refers to molecules identified from various environmental sources such a river beds, coral, plants, microorganisms and insects.

These types of modifications may be important to stabilize the subject polypeptide if administered to an individual or for use as a diagnostic reagent.

Other derivatives contemplated by the present invention include a range of glycosylation variants from a completely unglycosylated molecule to a modified glycosylated molecule. Altered glycosylation patterns may result from expression of recombinant molecules in different host cells.

The present invention further contemplates genetic sequences encoding the subject WARP. Such genetic sequences are referred to herein as WARP.

According to this embodiment, there is provided an isolated nucleic acid molecule comprising a sequence of nucleotides encoding or complementary to a sequence encoding a polypeptide which in situ forms part of the ECM in an animal wherein said nucleotide sequence comprises a sequence substantially as set forth in SEQ ID NO:1 or its complementary form or a nucleotide sequence having at least about 65% similarity thereto or a nucleotide sequence capable of hybridizing to SEQ ID NO:1 or its complementary form under low stringency conditions.

Another example of a nucleotide sequence encompassed by the above is the nucleotide sequence substantially set forth in SEQ ID NO:7.

In one preferred embodiment, the nucleic acid molecule is a murine WARP such as the nucleic acid molecule defined by SEQ ID NO:3.

In another embodiment, the nucleic acid molecule is a human WARP such as the nucleic acid molecule defined by SEQ ID NO:5.

Accordingly, another aspect of the present invention provides an isolated nucleic acid molecule comprising a sequence of nucleotides encoding or complementary to a sequence encoding a murine WARP or a derivative or homolog thereof, said nucleotide sequence substantially as set forth in SEQ ID NO:3 or its complementary form or a nucleotide sequence having at least about 65% similarity thereto or a nucleotide sequence capable of hybridizing to SEQ ID NO:3 or its complementary form under low stringency conditions.

In another embodiment, the present invention is directed to an isolated nucleic acid molecule comprising a sequence of nucleotides encoding or complementary to a sequence encoding a human WARP or a derivative or homolog thereof, said nucleotide sequence substantially as set forth in SEQ ID NO:5 or its complementary form or a nucleotide sequence having at least about 65% similarity thereto or a nucleotide sequence capable of hybridizing to SEQ ID NO:5 or its complementary form under low stringency conditions.

The subject nucleic acid molecule may be DNA (e.g. cDNA or genomic DNA) or RNA (e.g. mRNA) or be an RNA:DNA hybrid. Furthermore, the nucleic acid molecule may have nucleotide analogs inserted to facilitate resistance, for example, to nucleases. The nucleotide sequence of the genomic clone of human WARP is represented in SEQ ID NO:19 and is encompassed by the invention. The cDNA sequence encoding WARP and its corresponding amino acid sequence are represented in SEQ ID NOS:5 and 6, respectively.

The nucleic acid molecule may be linear, single or double stranded or in a covalently closed, circular form.

In a particularly useful embodiment, the nucleic acid molecule is in a vector or plasmid such as but not limited to an expression vector. The use of vectors is a particularly convenient means of producing recombinant forms of the subject WARP.

According to this embodiment, there is provided a method for producing a recombinant WARP, said method comprising introducing a nucleic acid molecule comprising the nucleotide sequence set forth in SEQ ID NO:3 or SEQ ID NO:5 or their complementary forms or a nucleotide sequence having at least about 65% similarity to SEQ ID NO:3 or SEQ ID NO:5 or their complementary forms or a nucleotide sequence capable of hybridizing to SEQ ID NO:3 or SEQ ID NO:5 or their complementary forms under low stringency conditions into a cell, culturing the cell or population of cells under conditions sufficient to permit expression of said nucleic acid molecule and then recovering the recombinant polypeptide.

This aspect of the present invention extends to derivatives and homologs of the subject nucleic acid molecules such as nucleic acid molecules encoding functional portions of the instant WARP. One example of a functional portion is a portion capable of interacting with another polypeptide or protein.

Although the present invention is particularly exemplified in relation to nucleic acid molecules defined by SEQ ID NO:3 or SEQ ID NO:5, the present invention extends to other related nucleic acid molecules which encode WARPs in the ECM. Such nucleic acid molecules are conveniently located by homology searching of particular databases.

According to this embodiment, there is provided a method of identifying a nucleotide sequence likely to encode a WARP, said method comprising interrogating an animal genome database conceptually translated into different reading frames with an amino acid sequence defining a VA domain and identifying a nucleotide sequence corresponding to a sequence encoding said VA domain.

Preferably, the genome is conceptually translated into from about 3 to about 6 reading frames and more preferably 6 reading frames.

The VA domain amino acid sequence may come from any convenient source such as but not limited to the 200 amino acid sequence of the α3(VI) N8 VA domain of human collagen VI. Interrogation also may be by any convenient means such as using the tblastn (v2.0) program.

Alternatively, hybridization may be used to interrogate genomic or cDNA clones to identify related nucleotide sequences.

WARPs and their genetic sequences have a range of therapeutic and diagnostic utilities. For example, any compromise in the integrity of the ECM may result in WARP or fragments thereof being detected in circulatory or tissue fluid such as blood, urine, synovial or lymph fluid. The detection of a WARP or fragments thereof would be indicative of a degenerative or disease condition, trauma or infection. Examples of various conditions include autoimmune disease, arthritis, sporting injuries, osteoporosis and various bone disorders. The detection of WARP in ECM and in particular cartilage is also indicative of normal ECM development. Accordingly, subjects may be tested in utero or post-natally for the presence of the WARP in the ECM to determine that ECM is developing correctly and is maintaining its integrity. Detection of the WARP in the ECM is also a useful monitor of regeneration of ECM following, for example, trauma or disease. Reference to "subjects" and "animal subjects" includes "human subjects".

The detection of mutations in WARP or WARP is proposed to be particularly useful in monitoring or diagnosing inherited cartilage disease, serving as a sensitive indicator of cartilage cell differentiation or another disease conditions (e.g. arthritis), or serving as an indicator that a propensity for such conditions to develop. Consequently, levels of WARP or mutations in WARP or WARP are useful in monitoring repair, regeneration or other disease processes, in addition to monitoring the onset or progression of arthritis and other conditions.

In addition, WARP may be useful in facilitating the "imprinting" of stem cells which, following proliferation or further differentiation, could be useful in tissue replacement therapy, for example, cartilage tissue. In this embodiment, stem cells may be derived from bone marrow, retina (e.g. astrocytes), spinal tap (e.g. neural stem cells), chord blood, adipose tissue or stein. These stem cells are removed, exposed to WARP and then proliferated and/or further differentiated, prior to being injected into damaged cartilage tissue. Alternatively or in addition, embryonic stem cells or other stem cells could be fused to cartilage cells or cells producing WARP in order to direct the differentiation of the stem cells to become cartilage cells.

Another aspect of the present invention contemplates a method of detecting a loss of ECM integrity in an animal subject, said method comprising screening body fluid from said animal for the presence of a WARP or fragment thereof wherein the presence of said WARP or fragment is indicative of a loss of ECM integrity.

In a related embodiment, there is contemplated a method for monitoring repair, regeneration or other disease processes in an animal subject, said method comprising screening body fluid from said animal for the presence of a WARP or fragment thereof wherein the presence of WARP or a particular level of WARP relative to normal controls is indicative of cartilage cell differentiation or the integrity of the cartilage or the predisposition or presence of a disease condition.

In another embodiment, the present invention provides a method for detecting a disease condition or a propensity for the development of a disease condition in an animal subject, said method comprising screening for a mutation in WARP or WARP wherein the presence of said mutation is indicative of a likelihood of a disease condition developing or a likelihood of the presence of a disease condition.

An example of a disease condition is arthritis or cartilage disease. An "animal" in this context includes a human. A "mutation" includes an amino acid substitution, deletion and/or insertion or a nucleotide substitution, deletion and/or insertion.

Any number of detection methods may be employed. Immunological testing, however, is particularly convenient. Accordingly, the present invention extends to antibodies and other immunological agents directed to or preferably specific for said WARP or a fragment thereof. The antibodies may be monoclonal or polyclonal or may comprise Fab fragments or synthetic forms.

Specific antibodies can be used to screen for the subject WARP and/or their fragments. Techniques for the assays contemplated herein are known in the art and include, for example, sandwich assays and ELISA.

It is within the scope of this invention to include any second antibodies (monoclonal, polyclonal or fragments of antibodies or synthetic antibodies) directed to the first mentioned antibodies referred to above. Both the first and second antibodies may be used in detection assays or a first antibody may be used with a commercially available anti-immunoglobulin antibody. An antibody as contemplated herein includes any antibody specific to any region of the WARP.

Both polyclonal and monoclonal antibodies are obtainable by immunization with a WARP or antigenic fragments thereof and either type is utilizable for immunoassays. The methods of obtaining both types of sera are well known in the art. Polyclonal sera are less preferred, but are relatively easily prepared. The preparation involves injection of a suitable laboratory animal with an effective amount of subject polypeptide, or antigenic parts thereof, collection of serum from the animal and isolation of specific sera by any of the known immunoadsorbent techniques. Although antibodies produced by this method are utilizable in virtually any type of immunoassay, they are generally less favored because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Another aspect of the present invention contemplates, therefore, a method for detecting a WARP or fragment thereof in a biological sample from a subject, said method comprising contacting said biological sample with an antibody specific for said WARP or fragment thereof or its derivatives or homologs for a time and under conditions sufficient for an antibody-polypeptide complex to form, and then detecting said complex.

The presence of the instant WARP or its fragment may be accomplished in a number of ways such as by Western blotting and ELISA procedures. A wide range of immunoassay techniques are available as can be seen by reference to U.S. Pat. Nos. 4,016,043, 4,424,279 and 4,018,653.

Sandwich assays are among the most useful and commonly used assays and are favored for use in the present invention. A number of variations of the sandwich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent. In accordance with the present invention, the sample is one which might contain a subject polypeptide including by tissue biopsy, blood, synovial fluid and/or lymph. The sample is, therefore, generally a biological sample comprising biological fluid.

In the typical forward sandwich assay, a first antibody having specificity for the instant polypeptide or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or where more convenient, overnight) and under suitable conditions (e.g. for about 20° C. to about 40° C.) to allow binding of any subunit present in the antibody. Following the incubation period, the antibody subunit solid phase is washed and dried and incubated with a second antibody specific for a portion of the hapten. The second antibody is linked to a reporter molecule which is used to indicate the binding of the second antibody to the hapten.

An alternative method involves immobilizing the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

"Reporter molecule," as used in the present specification, means a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e., radioisotopes) and chemiluminescent molecules. In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescene and EIA techniques are both very well established in the art and are particularly preferred for the present method. However, other reporter molecules, such as radioisotope, chemiluminescent or bioluminescent molecules, may also be employed.

The present invention also contemplates genetic assays such as involving PCR analysis to detect RNA expression products of a genetic sequence encoding a WARP. The genetic assays may also be able to detect nucleotide polymorphisms or other substitutions, additions and/or deletions in the nucleotide sequence of WARP. Changes in levels of WARP expression such as following mutations in the promoter or regulatory regions or loss of WARP activity following mutations in WARP nucleotides is proposed to be indicative of a disease condition or a propensity for a disease condition to develop. For example, a cartilage biopsy could be obtained and DNA or RNA. Alternative methods or methods which may be used in conjunction include direct nucleotide sequencing or mutation scanning such as single stranded conformation polymorphoms analysis (SSCP) as well as specific oligonucleotide hybridization, denaturing high performance liquid chromatography, first nucleotide change (FNC) amongst others.

The present invention further contemplates kits to facilitate the rapid detection of WARPs or their fragments in a subject's biological fluid.

Still yet another aspect of the present invention contemplates genomic sequences, including gene sequences encoding a WARP, as well as regulatory regions, such as promoters, terminators and transcription/translation enhancer regions associated with the gene encoding a WARP.

The term "gene" is used in its broadest sense and includes cDNA corresponding to the exons of a gene. Accordingly, reference herein to a "gene" is to be taken to include:—
  (i) a classical genomic gene consisting of transcriptional and/or translational regulatory sequences and/or a coding region and/or non-translated sequences (i.e., introns, 5'- and 3'-untranslated sequences); or
  (ii) mRNA or cDNA corresponding to the coding regions (i.e., exons) and 5'- and 3'-untranslated sequences of the gene.

The term "gene" is also used to describe synthetic or fusion molecules encoding all or part of an expression product. In particular embodiments, the term "nucleic acid molecule" and "gene" may be used interchangeably.

In a particularly useful embodiment, the present invention provides a promoter for the WARP gene. The identification of the promoter permits ECM and in particular cartilage-specific expression of particular genetic sequences. The latter would include a range of therapeutic molecules such as cytokines, growth factors, antibiotics or other molecules to assist in the treatment of disease, trauma or other conditions of the ECM.

Accordingly, another aspect of the present invention provides a cartilage-specific promoter or functional derivative or homolog thereof, said promoter in situ operably linked to a nucleotide sequence comprising SEQ ID NO:3 or SEQ ID NO:5 or their complementary forms or a nucleotide sequence having at least about 65% similarity to SEQ ID NO:3 or SEQ ID NO:5 or their complementary forms or a nucleotide sequence capable of hybridizing to SEQ ID NO:3 or SEQ ID NO:5 or their complementary forms under low stringency conditions.

The promoter is conveniently resident in a vector which comprises unique restriction sites to facilitate the introduction of genetic sequences operably linked to said promoter.

The present invention further contemplates a genetically modified animal.

More particularly, the present invention provides an animal model useful for screening for agents capable of ameliorating the effects of compromised ECM and in particular cartilage. In one embodiment, the animal model produce low amounts of WARP. Such an animal would have a predisposition for ECM-mediated diseases. Such an animal model is useful for screening for agents which ameliorate such conditions.

Accordingly, another aspect of the present invention provides a genetically modified animal wherein said animal produces low amounts of WARP relative to a non-genetically modified animal of the same species.

Preferably, the genetically modified animal is a mouse, rat, guinea pig, rabbit, pig, sheep or goat. More preferably, the genetically modified animal is a mouse or rat. Most preferably, the genetically modified animal is a mouse.

Accordingly, a preferred aspect of the present invention provides a genetically modified mouse wherein said mouse produces low amounts of WARP relative to a non-genetically modified mouse of the same strain.

The animal model contemplated by the present invention comprises, therefore, an animal which is substantially incapable of producing a WARP. Generally, but not exclusively, such an animal is referred to as a homozygous or heterozygous WARP-knockout animal. Such animals exhibit ECM-mediated disease conditions. These animals are useful for screening for agents which ameliorate such conditions and which can reduce the clinical severity of the disease condition. Once such molecules are identified, a treatment or prophylactic protocol can be developed which targets these conditions.

The animal models of the present invention may be in the form of the animals or may be, for example, in the form of embryos for transplantation. The embryos are preferably maintained in a frozen state and may optionally be sold with instructions for use.

The genetically modified animals may also produce larger amounts of WARP. For example, over expression of normal WARP or mutant WARP may produce dominant negative effects and may become useful disease models.

Accordingly, another aspect of the present invention is directed to a genetically modified animal over-expressing genetic sequences encoding WARP.

A genetically modified animal includes a transgenic animal, or a "knock-out" or "knock-in" animal.

Yet another aspect of the present invention provides a targeting vector useful for inactivating a gene encoding WARP said targeting vector comprising two segments of genetic material encoding said WARP flanking a positive selectable marker wherein when said targeting vector is transfected into embryonic stem (ES) cells and the marker selected, an ES cell is generated in which the gene encoding said WARP is inactivated by homologous recombination.

Preferably, the ES cells are from mice, rats, guinea pigs, pigs, sheep or goats. Most preferably, the ES cells are from mice.

Still yet another aspect of the present invention is directed to the use of a targeting vector as defined above in the manufacture of a genetically modified animal substantially incapable of producing WARP.

Even still another aspect of the present invention is directed to the use of a targeting vector as defined above in the manufacture of a genetically modified mouse substantially incapable of producing WARP.

Preferably, the vector is DNA. A selectable marker in the targeting vector allows for selection of targeted cells that have stably incorporated the targeting DNA. This is especially useful when employing relatively low efficiency transformation techniques such as electroporation, calcium phosphate precipitation and liposome fusion where typically fewer than 1 in 1000 cells will have stably incorporated the exogenous DNA. Using high efficiency methods, such as microinjection into nuclei, typically from 5-25% of the cells will have incorporated the targeting DNA; and it is, therefore, feasible to screen the targeted cells directly without the necessity of first selecting for stable integration of a selectable marker. Either isogenic or non-isogenic DNA may be employed.

Examples of selectable markers include genes conferring resistance to compounds such as antibiotics, genes conferring the ability to grow on selected substrates, genes encoding proteins that produce detectable signals such as luminescence. A wide variety of such markers are known and available, including, for example, antibiotic resistance genes such as the neomycin resistance gene (neo) and the hygromycin resistance gene (hyg). Selectable markers also include genes conferring the ability to grow on certain media substrates such as the tk gene (thymidine kinase) or the hprt gene (hypoxanthine phosphoribosyltransferase) which confer the ability to grow on HAT medium (hypoxanthine, aminopterin and thymidine); and the bacterial gpt gene (guanine/xanthine phosphoribosyltransferase) which allows growth on MAX medium (mycophenolic acid, adenine and xanthine). Other selectable markers for use in mammalian cells and plasmids carrying a variety of selectable markers are described in Sambrook et al., Molecular Cloning—A Laboratory Manual, Cold Spring Harbour, N.Y., USA, 1990.

The preferred location of the marker gene in the targeting construct will depend on the aim of the gene targeting. For example, if the aim is to disrupt target gene expression, then the selectable marker can be cloned into targeting DNA corresponding to coding sequence in the target DNA. Alternatively, if the aim is to express an altered product from the target gene, such as a protein with an amino acid substitution, then the coding sequence can be modified to code for the substitution, and the selectable marker can be placed outside of the coding region, for example, in a nearby intron.

The selectable marker may depend on its own promoter for expression and the marker gene may be derived from a very different organism than the organism being targeted (e.g. prokaryotic marker genes used in targeting mammalian cells). However, it is preferable to replace the original promoter with transcriptional machinery known to function in the recipient cells. A large number of transcriptional initiation regions are available for such purposes including, for example, metallothionein promoters, thymidine kinase promoters, β-actin promoters, immunoglobulin promoters, SV40 promoters and human cytomegalovirus promoters. A widely used example is the pSV2-neo plasmid which has the bacterial neomycin phosphotransferase gene under control of the SV40 early promoter and confers in mammalian cells resistance to G418 (an antibiotic related to neomycin). A number of other variations may be employed to enhance expression of the selectable markers in animal cells, such as the addition of a poly(A) sequence and the addition of synthetic translation initiation sequences. Both constitutive and inducible promoters may be used.

The DNA is preferably modified by homologous recombination. The target DNA can be in any organelle of the animal cell including the nucleus and mitochondria and can be an intact gene, an exon or intron, a regulatory sequence or any region between genes.

Homologous DNA is a DNA sequence that is at least 70% identical with a reference DNA sequence. An indication that two sequences are homologous is that they will hybridize with each other under stringent conditions (Sambrook et al., 1990, supra).

The present invention further contemplates co-suppression (i.e., sense suppression) and antisense suppression to down-regulate expression of WARP. This would generally occur in a target test animal such as to generate a disease model.

The present invention is further described by the following non-limiting Examples.

EXAMPLES

Example 1

Identification of WARP cDNAs

The mouse EST database was conceptually translated into six reading frames and interrogated with the 200 amino acid sequence of the α3(VI) N8 VA domain of human collagen VI (Chu et al., 1990, supra) using the tblastn program (v2.0) at the National Center for Biotechnology Information (NCBI).

Several overlapping cDNA clones with significant similarity to α3(VI) N8 at the protein level were identified. The inventors obtained three of these clones, ui42d08, ue22e08 and ml15f02 from E12.5 mouse embryo, spleen and kidney, respectively (Genome Systems). DNA sequencing (Amplicycle sequencing kit, Perkin Elmer Biosystems) revealed that clones ue22e08 (1026 bp) and mt15f02 (551 bp) lie entirely within the ui42d08 (2308 bp) sequence and exactly matched the larger clone spanning nucleotides 1282-2308 and 1833-2227, confirming that the three cDNAs represent a single gene.

Example 2

WARP Plasmid Constructs and Expression in Transfected Cells

The ui42d08 cDNA in pME18 (GenBank Accession number AI115125) (FIG. 1A) was subcloned into the pBluescriptSK-vector (Stratagene) as a Xho1 fragment. The clone was then sequenced using the Amplicycle sequencing kit (Perkin Elmer Biosystems) and translated in vitro using the TNT Coupled Transcription and Translation System (Promega) (Chan et al., J. Biol. Chem. 271: 13566-13572, 1996) to confirm the open reading frame. To generate a WARP GST-VA domain fusion construct, the mouse VA domain sequence from amino acid 21-212 was amplified by PCR using primers that anneal in the cDNA sequence between nucleotides 92-111 and 648-666. The primers were designed to include flanking BamH1 and EcoR1 sites to allow in-frame cloning of the VA domain PCR product into the glutathione S-transferase fusion vector pGEX-2T (Amersham Pharmacia). To enable immunoprecipitation of WARP protein from transfected cells, a His-tagged full-length expression construct was also produced. Six histidine residues were incorporated at the N-terminus immediately following amino acid 21, between the signal peptide and the start of the VA domain, by strand overlap extension PCR (Chan et al., 1996, supra) and subcloned into the pBluescriptSK-vector. To allow episomal expression in mammalian cells, WARP-His was subcloned from pBluescriptSK—into pCEP4 (InVitrogen) as a Xho1 fragment. WARP-His in pCEP4 was transfected into 293-EBNA cells (InVitrogen) grown in Dulbecco's Modified Eagles Medium (DMEM) containing 10% v/v bovine serum using FuGene transfection reagent (Boehringer Mannheim) according to the manufacturer's instructions and grown for 14 days in the presence of 250 μg/ml hygromycin B (Boehringer Mannheim) to select for transfected cells.

Example 3

Cell Culture

Human embryonic kidney 293-EBNA cells, mouse MC3T3 osteoblast (Sudo et al., J. Cell. Biol. 96: 191-198, 1983), Mov13 fibroblast (Schnieke et al., Nature 304: 315-320, 1983), C2C12 myoblast (McMahon et al., Am. J. Physiol. 266: 1795-1802, 1994), C57 primary fibroblast and MCT chondrocyte cell lines were maintained in culture in DMEM containing 10% v/v bovine serum. Primary chondrocytes were isolated as previously described (Chan et al., J. Biol. Chem. 268: 15238-15245, 1993). Briefly, rib cages were dissected from newborn mice and incubated in DMEM containing 5% v/v bovine serum and 2 mg/ml collagenase (Worthington Biochemical Corp.) for 30 mins at 37° C. Loose connective tissue and bone was removed and the rib cartilage incubated in fresh collagenase solution for 16 hrs. Chondrocytes released from cartilage were either centrifuged to pellet cells or plated out as a monolayer in a 60-mm dish. Pelleted cells, which retained a chondrocyte phenotype, were grown in DMEM containing 10% w/v fetal calf serum for 16 hrs prior to RNA isolation. Cells grown as a monolayer were cultured for 48 hrs prior to RNA isolation to allow chondrocyte de-differentiation (Chan et al., 1993, supra). Mouse MCT chondrocytes, immortalized with a temperature sensitive SV-40 large T-antigen (Lefebvre et al., J. Cell Biol. 128: 239-245, 1995), were cultured at the permissive temperature of 32° C., where the cells proliferate and express an osteoblast-like phenotype as demonstrated by expression of the osteoblast markers type I collagen and bone Gla protein. When grown at the non-permissive temperature of 37° C., the cells cease dividing and express type X collagen, matrix Gla protein and osteopontin, which are markers of hypertrophic chondrocytes. For one experiment MCT cells were grown at 37° C. for 3 days to induce a hypertrophic-like phenotype then transferred to 32° C. for 3 days to induce an osteoblast-like phenotype.

Example 4 mRNA Expression Analysis

Total RNA was isolated from mouse cell lines and primary rib chondrocytes using the mini Rneasy® RNA isolation kit (Qiagen) according to the manufacturer's instructions and from mouse tissues using the guanidinium thiocyanate and phenol/chloroform method of Chomzynski and Sacchi (Anal. BioChem. 162: 156-159, 1987). To ensure that no genomic DNA was carried through the isolation procedure all RNA samples were digested with DNA-free™ DNase Treatment and Removal kit (Ambion) and repurified using the Rneasy® kit. Each sample was then assessed for genomic DNA contamination by performing a RT-PCR reaction in the absence of reverse transcriptase. WARP mRNA expression was determined by Northern blot analysis, RT-PCR and semi-quantitative RT-PCR. For Northern blot analysis, 60 μg of total RNA was poly(A)-selected using oligo dT Dynabeads (Dynal), fractionated on a 1% w/v agarose formaldehyde gel and transferred to Hybond N+ nylon membrane (Amersham). A $[^{32}P]$-dCTP-labeled WARP probe was hybridized to the blot in Ultrahyb hybridization solution (Ambion) at 42° C. overnight. The blot was washed to a stringency of 0.1×SSC/0.1% w/v SDS at 65° C. and subjected to autoradiography. RT-PCR was performed using the GeneAmpR RNA PCR kit (Perkin Elmer). Two μg of total RNA was added to each RT reaction in a total volume of 40 μl and 10 μl of cDNA was used in the subsequent PCR in a 50 μl reaction volume. The optimal Mg2+ concentration was found to be 0.35 mM for the WARP amplification and 1 mM for the internal control, hypoxanthine guanine phosphoribosyltransferase (HPRT), a housekeeping gene involved in purine metabolism. In the PCR step, NR1 [$1666$5'-CTCAAAGCCATGCGTAGTCC-3'$1685$ (SEQ ID NO:9)], and NF4 [$953$5'-AGAACGCATCGT-CATCTCGC-3'$^{972}$ (SEQ ID NO:10)] primers were used to amplify a 693 bp region of WARP. mHPRT1 [$^{23}$5'-CCT-GCTGGATTACATTAAAG-3'$^{251}$ (SEQ ID NO:11)] and mHPRT2 [$^{581}$5'-TCAAGGGCATATCCAACAAC-3'$^{601}$ (SEQ ID NO:12)] primers were used to amplify a 350 bp fragment of the mouse HPRT gene (GenBank Accession Number NM_013556). The cycle number for each gene was selected so that amplification was in the linear range, allowing the level of PCR products to be compared between samples. Simultaneous amplification of HPRT derived from the same cDNA reaction allowed correction for small variations in amount of template. For RT-PCR, primers and probes were designed with Primer Express (v1.0) software according to Applied Biosystems guidelines, and obtained directly from Applied Biosystems. The fluorophores, carboxyfluorescein (FAM) and VIC™ were added to the 5' end of WARP and HPRT probes respectively, and the N,N,N',N'-tetramethyl-6-carboxyrhodamine (TAMRA) fluorophore added to the 3' end of both probes during synthesis. The WARP probe [5'-(FAM)-CTGGTCATCGCCGCCCTTGC-(TAMRA)-3' (SEQ ID NO:13)] and primers [$^{1399}$5'-GACCAGCGTTAATTC-CTTTCGT-3' (SEQ ID NO:14) and 5'-CCGGGTTTCCCG-GAAGT-3'$^{1472}$ (SEQ ID NO:15) amplified a 73 bp region. The HPRT probe [5'-(VIC)-TTACTGGCAACATCAACAG-GACTCCTCGTATT-(TAMRA)-3' (SEQ ID NO:16)] and primers [$^{739}$5'-CCACAGGACTAGAACACCTGCTAA-3' (SEQ ID NO:17) and 5'-CCTAAGATGAGCGCAAGT-TGAA-3'$^{825}$ (SEQ ID NO:18) amplified an 86 bp region. In the intact probe, TAMRA is able to quench FAM and VIC™, but during the PCR the reporter fluorophores are released into solution by the 5'-exonuclease activity of the polymerase allowing them to fluoresce. The amount of fluorescence is directly proportional to the amount of specific product generated in the PCR. Reactions were performed on a Perkin Elmer Life Sciences ABI PRISM 7700 Sequence Detector using the TaqMan Universal PCR master mix (Applied Biosystems) containing AmpliTaq Gold polymerase and repeated several times with similar results. The data are expressed as a ratio of WARP:HPRT mRNA at a cycle number that falls within the linear range of amplification as determined by visual examination of the data generated by Sequence Detector (v1.7) software (Applied Biosystems).

Example 5

Production of an Anti-WARP Antibody

The GST-VA fusion cDNA construct in pGEX-2T was transformed into competent DH5α bacteria, individual colonies grown and fusion protein expression induced by IPTG [Kaelin, 1992 #2561]. The insoluble fusion protein was purified from cell preparations using a Mini Whole Gel Eluter Harvester (BioRad) and injected into a NZ White rabbit. Antisera from the rabbit immunized with purified GST-VA domain fusion protein bound to the fusion protein in a dose dependent manner in an ELISA assay. To demonstrate specificity of the antibody for WARP, the fusion protein was cleaved with thrombin to separate the GST and VA domains and subjected to immunoblotting using the antisera as probe. The antisera recognized both GST and the VA domain at a dilution of 1 in 1000.

Example 6

Cartilage Sample Preparation and Western Blotting

Joint and rib tissue was dissected from newborn mice and cleaned of surrounding bone and connective tissue. Cartilage samples were powdered in a freezer mill (Spex) and dissolved in extraction solution 1 (40 mM Tris/HCl, pH 7.5, 10 mM EDTA containing 'Complete' protease inhibitors (Roche)). Samples were then vortexed and sonicated for 20 secs and the insoluble material pelleted in a microcentrifuge. The supernatant was collected and saved as soluble fraction 1 and the insoluble pellet washed and sonicated three times in Tris/HCl, pH 7.5, 10 mM EDTA. The pellet was resuspended in extraction solution 1 and treated overnight at 37° C. with 0.02 units of chondroitinase ABC (ICN) and 1 unit of hyaluronidase (Sigma). Samples were pelleted and washed three times with 40 mM Tris/HCl, pH 7.5, 10 mM EDTA and the supernatants saved as soluble fraction 2. The remaining pellet was dissolved in 6 M GuHCl, 40 mM Tris/HCl, pH 7.5, 10 mM EDTA containing protease inhibitors for 5 hrs at 4° C., then centrifuged. The supernatant was saved as soluble fraction 3 and the matrix components precipitated with 95% v/v ethanol and the pellet washed with 70% v/v ethanol. Samples were then freeze-dried and resuspended in 200 µl of 8 M urea, 4% v/v cholamidopropyl-dimethylammonio-propane-sulfonate (CHAPS), 40 mM Tris-HCl, pH 7.5, containing 2 mM tributylphosphine and 2.5% v/v β-mercapto-ethanol. For some experiments the reducing agents were omitted.

The protein content of extracts 1, 2, and 3 was determined by the Bradford assay and 20 µg total protein aliquots were denatured by heating at 95° C. for 5 min, separated on a 10% w/v SDS-polyacrylamide gel and transferred to Immobilon™-P PVDF membrane (Millipore). The membrane was blocked in 5% w/v milk powder in PBS for 1 hr and then incubated in antibody buffer (0.5% w/v milk powder in 0.1% w/v Tween-20 in PBS) containing either WARP or matrilin-1 antisera (Paulsson, M. and Heinegard, D., BioChem. J. 207: 207-213, 1982) (1 in 1000 and 500 dilution, respectively) for 1 hr at room temperature. Following three washes in 0.1% w/v Tween-20 in PBS, anti-rabbit IgG-HRP secondary antibody (Dako Corporation) was added at a dilution of 1 in 10,000 in antibody buffer and incubated for 1 hr. Following washing, the signal was developed with ECL Plus Western blotting detection system (Amersham Pharmacia) and autoradiography performed using X-OMAT film (Kodak).

Example 7

WARP Biosynthetic Labeling and Analysis

293-EBNA cells transfected with WARP-His cDNAwere grown to confluence in a 60-mm dish and labeled for 16 hrs with 300 µCi of L-[$^{35}$S]-methionine (1398 Ci/mmol, NEN Research Products) in DMEM without L-methionine and L-cysteine (Life Technologies, Inc) as previously described (Fitzgerald et al., 2001, supra). The medium fraction was removed and clarified centrifuged and NP-40 added to the supernatant to 1% v/v together with a cocktail of protease inhibitors (1 mM 4-(2 aminoethyl)-benzenesulfonyl-flouride (AEBSF); 1 mM phenylmethylsulfonyl fluoride (PMSF); 20 mM N-ethylmaleimide (NEM)). The cell layer was dispersed in 1 ml of lysis buffer (150 mM NaCl; 50 mM Tris-HCl, pH 7.5; 5 mM EDTA; 20 mM NEM; 1 mM AEBSF; 1 mM PMSF; 1% v/v NP-40) on ice for 30 min., and then centrifuged briefly to remove insoluble material. Following a pre-clear step with 100 µl protein G-sepharose (20% w/v slurry in PBS), anti-His antibody (Boehringer Mannheim)(1 in 100 dilution) was added to each fraction together with 100 µl fresh protein G-sepharose and mixed gently at 4° C. for 16 hrs. The antibody-sepharose complex was washed twice with 50% w/v lysis buffer/50% w/v NET (150 mM NaCl; 50 mM Tris-HCl, pH 7.4; 1 mM EDTA; 0.1% w/v NP-40) for 30 min each then twice with NET. Immunoprecipitated material was separated from the sepharose beads by heating at 65° C. for 15 min in SDS-PAGE sample buffer containing 20 mM dithiothreitol (DTT), fractionated on a 10% w/v) SDS-polyacrylamide gel and subjected to fluorography.

Example 8

N-glycosidase Treatment

WARP-His protein was deglycosylated by N-glycosidase F (Roche) treatment according to the manufacturer's guidelines. Immunoprecipitated WARP-His was denatured by boiling in 1% w/v SDS for 2 min, diluted 1 in 10 with sodium phosphate buffer (20 mM sodium phosphate, pH 7.2; 10 mM sodium azide; 50 mM EDTA; 0.5% v/v NP-40), and boiled again for 2 min. Following addition of 0.4 units of N-Glycosidase F the sample was incubated for 20 hrs at 37° C. then heat denatured in sample buffer containing 20 mM DTT and analyzed by SDS-polyacrylamide gel electrophoresis.

Example 9

SDS-polyacrylamide Gel Electrophoresis

Samples were resolved on 10% w/v polyacrylamide separating gels with a 3.5% w/v acrylamide stacking gel in the absence of urea as described previously (Bateman et al., BioChem. J. 217: 103-115, 1984). Prior to electrophoresis, samples were diluted with loading buffer to give a final concentration of 0.125 mM Tris/HCl, pH 6.8 containing 2% w/v SDS and denatured for 10 min or otherwise indicated. Electrophoresis conditions and fluorography of radioactive gels have been described previously (Bateman et al., 1984, supra; Chan et al., 1996, supra).

Example 10

Identification of WARP Using Genomic Databases

To identify novel ECM proteins that contain VA-like domains, the mouse EST database at the NCBI was searched with the N-terminal N8 VA-domain of the α3 chain of human collagen VI (Chu et al., 1990, supra). The inventors identified several overlapping EST clones that when fully sequenced clearly represent a novel gene that contains a predicted VA-like protein module. The longest EST clone, ui42d08, appeared to be full-length with a start methionine codon at nucleotides 30-32 and an in-frame TGA stop codon at 1275-1277, indicating an open reading frame of 1248 bps with 29 bps of 5'UTR and 1063 bps of 3'UTR (refer to the WARP GenBank entry for cDNA sequence, #AAK38350). The 3' end of the clone includes a poly(A) tail and a predicted polyadenylation site at nucleotides 2279-2285. The full-length WARP cDNA was transcribed and translated in vitro and SDS-PAGE analysis demonstrated a single protein product indicating that no stop codons were present within the open reading frame. Since the full-length WARP nucleotide and protein sequences have not been previously reported and the VA-domain is related to, but distinctly different from, those described in existing family members (FIG. 2A), the inventors conclude that this gene is a new member of the VA superfamily. The inventors named this gene, WARP, for von Willebrand factor A-domain related protein.

The human homolog of WARP was identified by searching the genome data with the mouse WARP protein sequence. A match with a predicted protein sequence (hypothetical protein FLJ22215) with very high homology to the mouse WARP was found. The human WARP gene, which maps to chromosome 1p36.3 (contig NT_025635), is composed of four exons each of which encode a separate protein domain. The first exon (73 bps in size) encodes the signal peptide, exon 2 (558 bps) encodes the VA-domain, exon 3 (279 bps) encodes the first F3 repeat and exon 4 (347 bps) encodes the second F3 repeat, the P/R-rich C-terminal segment and the 3' untranslated region. These sequences are clearly homologs of each other because they share 79% amino acid identity (see FIG. 1C). In addition, if conserved changes are considered in the analysis, they share 95% identity.

The mouse WARP open reading frame encodes a 415 amino acid protein with a predicted molecular weight of 45 kDa although the human sequence is slightly larger with a 3 amino acid (PRP) insertion in the C-terminal domain (FIG. 1C). Both homologs contain an 18 amino acid signal sequence with a cleavage site between $Ala^{18}$ and $Arg^{19}$ as indicated by signal sequence prediction program SignalP (v2.0) (Nielsen et al., *Protein Engineering* 10: 1-6, 1997). The signal sequence is followed by a VA-domain of approximately 200 amino acids with a putative MIDAS motif (Lee et al., 1995, supra) and three potential O-linked sites at $Ser^{148}$, $Thr^{362}$ and $Thr^{401}$, as predicted by NetOGlyc software (Hansen et al., *BioChem. J.* 308: 801-813, 1995) although only the first two are conserved in the human sequence (FIG. 1C). Adjacent to the VA-domain are two fibronectin type III (F3) repeats of approximately 80 amino acids in length, each containing a potential N-linked glycosylation site at $Asn^{264}$ and $Asn^{359}$ that fits the consensus sequence NxS/T. The C-terminus at the end of the second F3 repeat is 21 amino acids in length (24 in the human sequence) and is rich in proline and arginine residues, but did not show homology to any other protein by extensive database searching. The domain structure of the WARP proteins is shown in FIG. 1B.

Example 11

Similarity fWARP to Other ECM Proteins

The protein sequences of the two domains present in WARP (VA and F3) were used to search the Non-Redundant and Conserved Domain databases at NCBI. A high degree of amino acid similarity exists between the WARP VA-domain and those found in other ECM proteins with most similarity to VA-domains present in the FACIT collagens XII, XIV (Ricard-Blum et al., In: Protein Profile Oxford University Press, Oxford, 2000) and the recently described FACIT collagens XX (Koch et al., 2001, supra) and XXI (Fitzgerald, J. and Bateman, J. F., *FEBS Lett.* 505: 275-280, 2001), the matrilins (Deak et al., 1999, supra) and cochlin (Robertson et al., 1997, supra) (FIG. 2A). The amino acids within the MIDAS motif which are critical for ion binding, $Asp^{40}$, $Ser^{42}$, $Ser^{44}$, $Thr^{113}$ and $Asp^{144}$ are conserved in both mouse and human WARP although biochemical and crystallographic studies are required to directly demonstrate a functional MIDAS motif. In addition, the overall arrangement of alpha helices and beta sheets that form the important secondary structural framework (Emsley et al., 1997, supra) shared between all VA-like domains is conserved in WARP. The two F3 repeats are less conserved than the VA-domain, although the overall framework of 7 hydrophobic strands that form the β-sandwich typical of F3 repeats is conserved (Leahy et al., 1996, supra) (FIG. 2B). The first F3 repeat, F3-1, is most similar to those found in tenascins and collagen XIV and F3-2 is most similar to those in collagen VII and the FACIT collagens.

Example 12

WARP mRNA is Expressed Highest in Chondrocytes

The WARP mRNA expression pattern in cell lines was examined by Northern blot analysis using poly(A) mRNA selected from primary rib chondrocytes, Mov13 fibroblasts, MC3T3 osteoblasts and C2C12 myoblasts (FIG. 3A). WARP mRNA was present in chondrocytes (lane 1), but not in the osteoblast, fibroblast and myoblast cell lines (lanes 2-4). WARP migrates as a 2.3 kb mRNA which is in agreement with the size of the full-length WARP cDNA represented by clone ui42d08 which is 2308 bp in size (see FIG. 1).

To examine the expression of WARP mRNA in a wider range of tissues, total RNA was isolated from mouse heart, skeletal muscle, testis, brain, and lung, and subjected to RT-PCR using primers specific for WARP and a control, HPRT (FIG. 3B). To control for variation between RT reactions, WARP and HPRT were amplified in separate reactions using the same template cDNA. Following 36 cycles of amplification, a WARP PCR product was present in chondrocyte RNA (upper panel, lane 6), but not in any other tissues or cell lines. The presence of a band representing HPRT in all lanes (lower panel) indicates that for all samples the starting RNA was intact and the RT reactions were successful.

To gain a reliable and semi-quantitative estimation of WARP mRNA levels in chondrocytes and cell lines, a third technique for assaying mRNA levels, Real-time PCR, was employed (FIG. 3C). In this method, a fluorescently-labeled probe, designed to anneal between two opposing primers, is removed by the action of the polymerase allowing an accurate estimation of PCR product levels by the appearance of a fluorescent signal in solution. By labeling each probe with a different fluorophore, the amplification reaction can be performed in the same tube. Thus, there is no need for controls to evaluate variations in amount of input cDNA and the efficiency of the amplification reaction between samples. The data are expressed as a ratio of WARP:HPRT mRNA at a cycle number that falls within the linear range of amplification. WARP mRNA levels were 7-fold higher in both primary rib chondrocytes and MCT cells induced to form a hypertrophic chondrocyte-like phenotype, than in MCT cells induced to form an osteoblast-like phenotype and MC3T3 osteoblasts. Expression in chondrocytes was >20-fold higher compared to fibroblasts cell lines and fibroblast-like cells derived from de-differentiated primary chondrocytes. These differences in the level of WARP expression are consistent with those detected by Northern analysis (FIG. 3A) and RT-PCR (FIG. 3B) and indicate that WARP is expressed highest in chondrocytes and at much lower levels in other tissues and cell lines.

These expression experiments demonstrate that WARP mRNA is expressed highest in primary rib chondrocytes which contain a mixed population of resting, proliferative, maturing and hypertrophic chondrocytes and in MCT cells induced to express a hypertrophic chondrocyte-like phenotype (Lefebvre et al., 1995, supra). WARP mRNA was undetected or expressed at very low levels in all other tissues and cell lines examined, including MCT cells induced to form osteoblast-like cells. Interestingly, WARP expression was down-regulated when rib chondrocytes were allowed to de-differentiate into fibroblast-like cells suggesting that expression is tightly controlled by the chondrocyte program of gene expression. This is supported by our finding that when MCT cells are induced to change from a hypertrophic-like to an osteoblast-like phenotype by changing the temperature of incubation from 37° C. to 32° C., WARP expression was reduced approximately 6-fold (FIG. 3C).

Example 13

WARP is an Oligomeric Glycoprotein In Vitro

Figure 4:
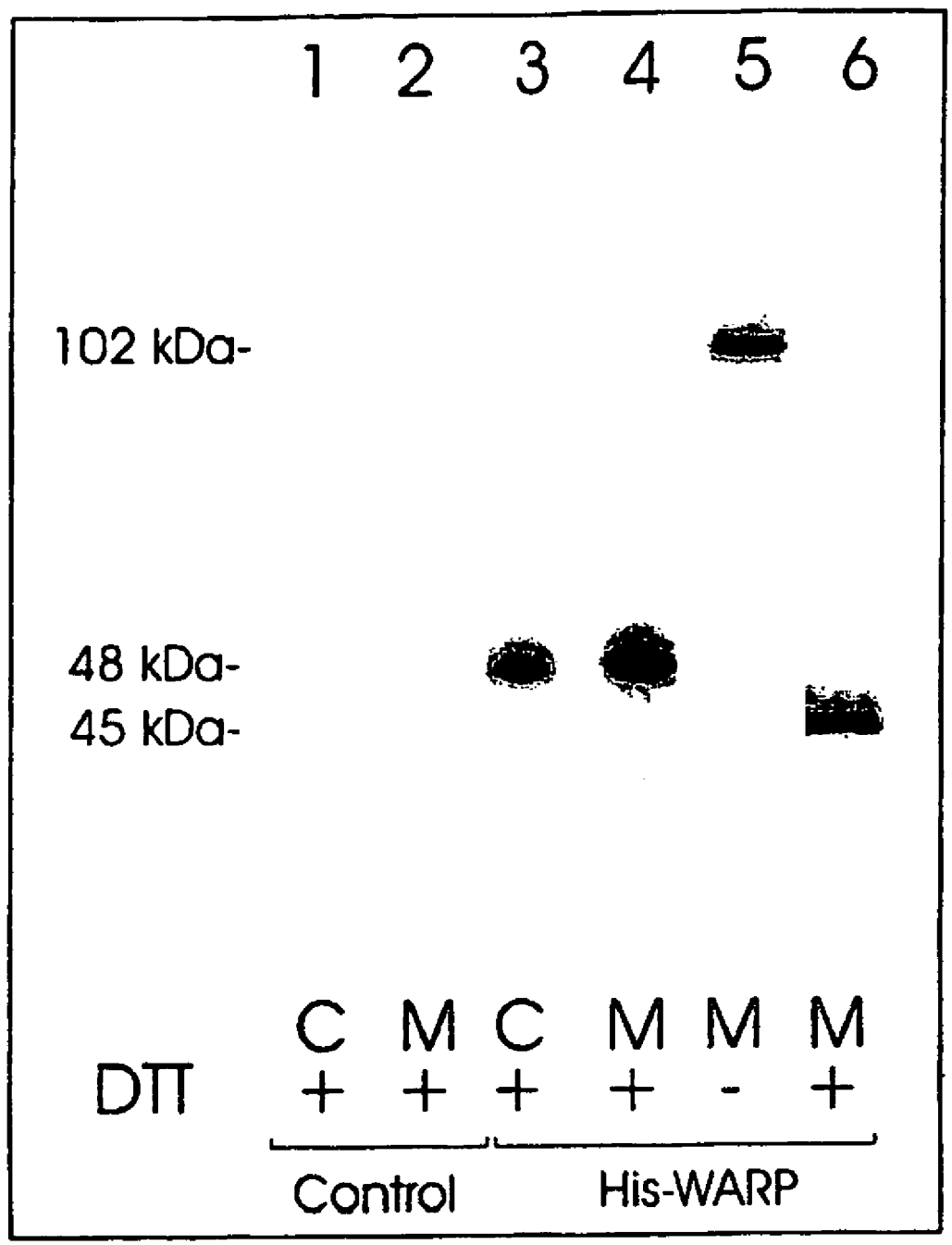
FIG. 4 is a representation showing that WARP is a secreted glycoprotein that forms oligomers in vitro. His-WARP cDNA in pCEP4 was transfected into 293-EBNA human embryonic kidney cells and His-WARP protein was immunoprecipitated from cell layer (lanes 1 and 3) and medium (lanes 2, 4-6) fractions of untransfected control 293-EBNA cells (control, lanes 1 and 2) or 293-EBNA cells transfected with His-WARP cDNA (His-WARP, lanes 3-6) using an anti-His antibody. Sample digested with N-Glycosidase F following immounopercipitation is shown in lane 6. All samples were reduced with 20 mM DTT prior to SDS-PAGE except for sample in lane 5. The migration position of protein molecular weight markers is indicated on the left.

To determine whether the predicted signal sequence is functional in directing WARP secretion from cells, and to determine if the putative N-glycosylation sites are utilized, a WARP cDNA expression construct with a poly-His tag inserted between the signal peptide and VA-domain was transfected into 293-EBNA cells. The stably transfected cells were labelled overnight with 35S-methionine and immunoprecipitated with anti-His antibodies. No material was immunoprecipitated from untransfected 293-EBNA cells (FIG. 4, lanes 1 and 2), indicating that no endogenous proteins are recognized by the anti-His antibody. In cells transfected with the His-WARP cDNA, His-tagged WARP protein migrated as an approximately 48 kDa band in both cell layer and media fractions (lanes 3 and 4). The majority of WARP is detected in the medium during these continuous labelling conditions, suggesting that WARP is efficiently secreted from cells and functions in the ECM environment. When the immunoprecipitated material was resolved under non-reducing conditions, a higher molecular weight form was present indicating that in these cells WARP forms higher-order structures via reducible disulfide bonds. The higher molecular weight species migrates at approximately 102 kDa, suggesting that WARP assembles into a disulfide-bonded homo-dimer. Although both human and mouse WARP protein sequences contain two C-terminal Cys residues, only one is conserved in both species at $Cys^{393}$. Site-directed mutagenesis experiments will determine which Cys residue participates in intermolecular disulfide bond formation. When WARP was subjected to N-glycosidase digestion there was a mobility shift to approximately 45 kDa indicating that WARP has one or more N-linked oligosaccharide side chains (lane 6). The molecular weight of the deglycosylated protein is in good agreement with the predicted molecular weight of 45 kDa. There are two possible N-glycosylation sites at Asn254 and Asn359 located in similar positions in the centre of each of the two F3 repeats in a loop region between β-strands C and C' (FIG. 2B). Although we might expect both sites to be equally available for glycosylation, the data does not provide information on whether one or both of these sites is glycosylated in vitro.

Example 14

WARP is an Oligomeric Protein Expressed in Cartilage

Figure 5:
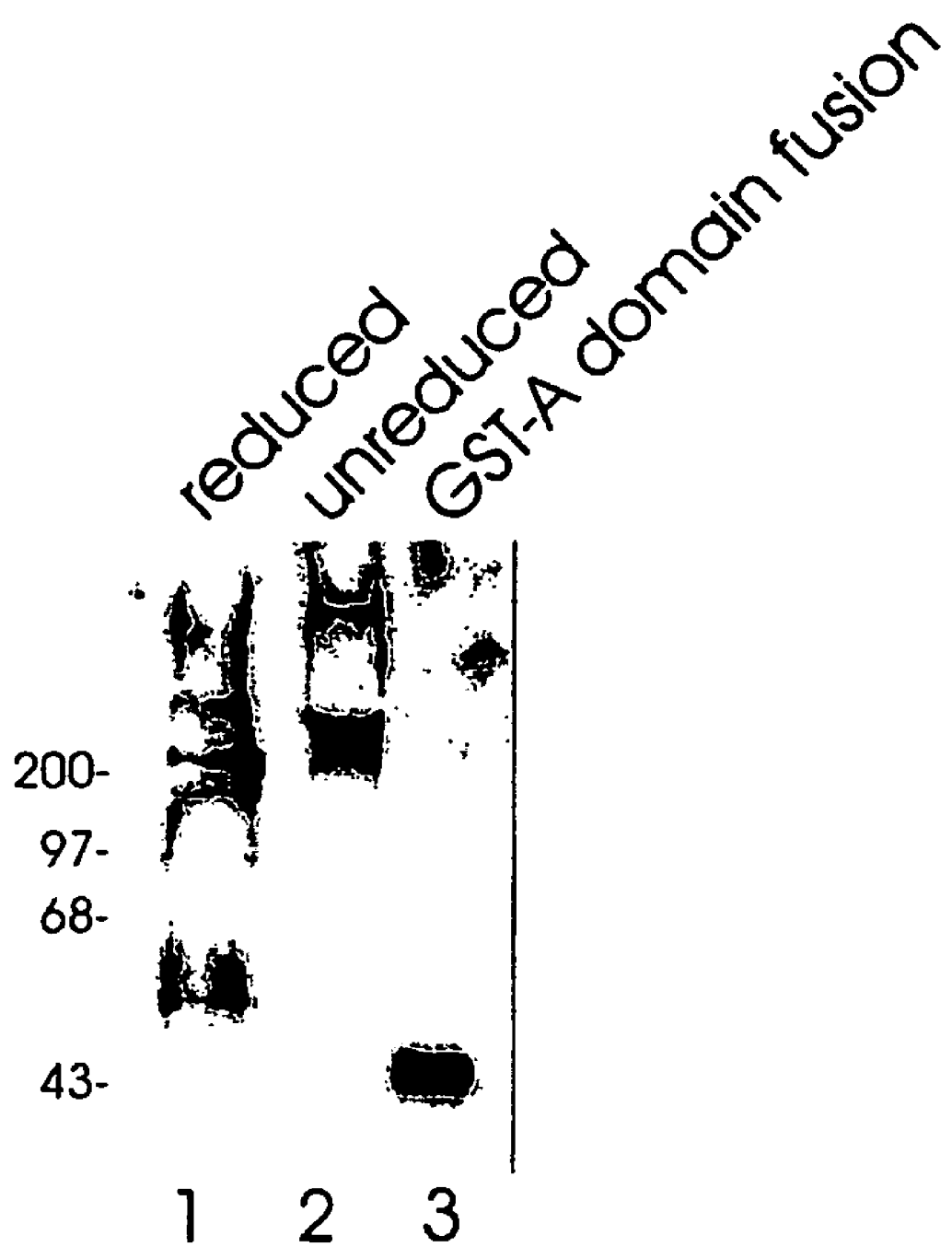
FIG. 5 is a photographic representation showing that WARP forms higher-order structures in vivo. Western blot showing WARP expression in guanidine-soluble extracts of newborn mouse cartilage. Lane 1, rib cartilage sample reduced with 2 mM tributylphosphine and 2.5% v/v β-mercapto-ethanol; lane 2, cartilage sample prepared and resolved in the absence of reducing agents; lane 3, 170 ng of GST-VA domain fusion protein. Lanes 1 and 2 contained 20 μg of protein per lane. WARP antibody used at a dilution of 1 in 1000. The migration position of the molecular weight markers is indicated on left.

To detect WARP protein in vivo, a polyclonal antibody against a bacterially expressed GST-VA domain fusion protein was made and used to probe an immunoblot containing serial extractions of newborn cartilage. To determine whether WARP exists as a monomer or forms higher-order structures in vivo, guanidine-soluble extracts were prepared from newborn mouse rib cartilage and subjected to SDS-PAGE analysis under reducing and non-reducing conditions and immunoblotted using WARP antisera (FIG. 5). When cartilage extracts were prepared and resolved under reducing conditions WARP migrated as a 50 kDa monomer (FIG. 5A, lane 4), although in some experiments there was also some higher-order oligomeric forms of WARP (FIG. 5, lane 1). These are presumably due to incomplete reduction or dissociation during sample preparation. In contrast, when the cartilage extract was prepared and fractionated in the absence of reducing agents, WARP was present exclusively as higher-order oligomers and there was a complete absence of 50 kDa monomeric WARP (lane 2). The WARP oligomer migrates as a smeared band (FIG. 5, lane 2), which may reflect variability in the numbers of WARP monomers in the oligomer, or possibly variation in the glycosylation pattern of WARP monomers which also demonstrate a diffuse electrophoretic migration (FIG. 5A, lane 4 and FIG. 5, lane 2). These experiments clearly demonstrate that endogenous WARP forms disulfide-bonded multimers of greater than 200 kDa in size, although it is not known whether these are composed of WARP homo-oligomers, or hetero-oligomers where WARP is disulfide bonded to other ECM proteins.

The C-terminus of matrilin-1 forms a coiled-coil structure composed of a heptad repeat of hydrophobic amino acids which directs the formation of matrilin multimers (Beck et al., *J. Mol. Biol.* 256: 909-923, 1996). Multimers are then stabilized by interchain disulfide bonds provided by two Cys residues present within the C-terminus (Haudenschild et al., *J. Biol. Chem.* 270: 23150-23154, 1995). The C-terminal domain in WARP is not predicted to form a coiled-coil structure of the type found in matrilins because it does not contain a well defined heptad repeat of hydrophobic residues. However, the C-terminal Cys residues, at $Cys^{369}$ and $Cys^{393}$ in the second F3 repeat, would be in a good position to stabilize WARP oligomerization and it is tempting to speculate that the C-terminus of WARP is involved in the formation of WARP oligomers.

The results clearly show that WARP is also found in the cartilage matrix in vivo, and the necessity for extraction with a chaotrophic agent suggests that it may be a strongly interacting matrix component. However, the experiments do not provide insight on whether WARP also exists in a number of pools of differing solubilities and possibly different functions during development or maturation. A proportion of WARP may also be present as insoluble supramolecular aggregates or covalently linked to guanidine-insoluble matrix components. These important questions will be addressed by further detailed biochemical analysis.

Example 15

Human WARP

A human homolog of murine WARP was identified by database homology searching. Nucleotide sequence (SEQ ID NO: 5) corresponds to amino acid sequence (SEQ ID NO:6).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The present invention is not to be limited in scope by the specific embodiments described herein, which are intended as single illustrations of individual aspects of the invention, and functionally equivalent methods and components are within the scope of the invention. Various publications are cited herein, the contents of which are hereby incorporated by reference in their entireties.

We claim:

1. An isolated polypeptide, wherein the polypeptide is a von Willebrand Factor A-Related Protein (WARP) comprising the entire amino acid sequence set forth in SEQ ID NO:6.

* * * * *

UNITED STATES PATENT AND TRADEMARK OFFICE
CERTIFICATE OF CORRECTION

PATENT NO. : 7,569,665 B2  Page 1 of 1
APPLICATION NO. : 10/699035
DATED : August 4, 2009
INVENTOR(S) : Bateman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 9 days.

Signed and Sealed this

Seventh Day of September, 2010

David J. Kappos
*Director of the United States Patent and Trademark Office*

SEQUENCE LISTING

```
<160> NUMBER OF SEQ ID NOS: 40

<210> SEQ ID NO 1
<211> LENGTH: 537
<212> TYPE: DNA
<213> ORGANISM: Homo sapiens

<400> SEQUENCE: 1
ggggacctga tgttcctgct ggacagctca gccagcgtct ctcactacga gttctcccgg      60
gttcgggagt ttgtggggca gctggtggct ccactgcccc tgggcaccgg ggccctgcgt     120
gccagtctgg tgcacgtggg cagtcggcca tacaccgagt tcccttcgg ccagcacagc      180 tcgggtgagg ctgcccagga tgcggtgcgt gcttctgccc agcgcatggg tgacacccac     240
actggcctgg cgctggtcta tgccaaggaa cagctgtttg ctgaagcatc aggtgcccgg     300
ccaggggtgc ccaaagtgct ggtgtgggtg acagatggcg gctccagcga ccctgtgggc     360 cccccatgc aggagctcaa ggacctgggc gtcaccgtgt tcattgtcag caccggccga     420
ggcaacttcc tggagctgtc agccgctgcc tcagcccctg ccgagaagca cctgcactt      480 gtggacgtgg atgacctgca catcattgtc caagagctga ggggctccat tctcgcg        537

<210> SEQ ID NO 2
<211> LENGTH: 180
<212> TYPE: PRT
<213> ORGANISM: Homo sapiens
```

<400> SEQUENCE: 2

```
Arg Gly Asp Leu Met Phe Leu Leu Asp Ser Ser Ala Ser Val Ser His
  1               5                  10                  15

Tyr Glu Phe Ser Arg Val Arg Glu Phe Val Gly Gln Leu Val Ala Pro
                 20                  25                  30

Leu Pro Leu Gly Thr Gly Ala Leu Arg Ala Ser Leu Val His Val Gly
             35                  40                  45

Ser Arg Pro Tyr Thr Glu Phe Pro Phe Gly Gln His Ser Ser Gly Glu
         50                  55                  60

Ala Ala Gln Asp Ala Val Arg Ser Ala Gln Arg Met Gly Asp Thr
 65                  70                  75                  80

His Thr Gly Leu Ala Leu Val Tyr Ala Lys Glu Gln Leu Phe Ala Glu
                 85                  90                  95

Ala Ser Gly Ala Arg Pro Gly Val Pro Lys Val Leu Val Trp Val Thr
            100                 105                 110

Asp Gly Gly Ser Ser Asp Pro Val Gly Pro Pro Met Gln Glu Leu Lys
            115                 120                 125

Asp Leu Gly Val Thr Val Phe Ile Val Ser Thr Gly Arg Gly Asn Phe
        130                 135                 140

Leu Glu Leu Ser Ala Ala Ser Ala Pro Ala Glu Lys His Leu His
145                 150                 155                 160

Phe Val Asp Val Asp Leu His Ile Ile Val Gln Glu Leu Arg Gly
                165                 170                 175

Ser Ile Leu Asp
            180

<210> SEQ ID NO 3
<211> LENGTH: 1266
<212> TYPE: DNA
<213> ORGANISM: Mus musculus

<400> SEQUENCE: 3
atgctgttct ggactgcgtt cagcatggct ttgagtctgc ggttggcatt ggcgcggagc      60
agcatagagc gcggttccac agcatcagac ccccaggggg acctgttgtt cctgttggac     120
agctcagcca gctgtcaca  ctatgagttc tcaagagttc gggaatttgt ggggcagctg     180
gtggctacga tgtctttcgg acccggggct ctgcgtgcta gtctggtgca cgtgggcagc     240
cagcctcaca cagagtttac ttttgaccag tacagttcag ccaggctat  acgggatgcc     300
atccgtgttg caccccaacg tatgggtgat accaacacag gcctggcact ggcttatgcc     360
aaagaacaat tgtttgctga ggaagcaggt gcccggccag gggttcccaa ggtgctggtg     420
tgggtgacag atggtggctc cagcgacccc gtgggccccc ctatgcagga gctcaaggac     480
ctgggtgtca ccatcttcat tgtcagcact ggccgaggca acctgttgga gctgttggca     540
gctgcctcgg ctcctgccga aaagcaccta cactttgtgg atgtggatga tcttcctatc     600
attgcccggg agctgcgggg ctccataact gatgcgatgc agccacaaca gcttcatgcc     660
tcggaggttc tgtccagtgg cttccgcctg tcctggccgc cctgctgac  agcggactct     720
ggttactacg tgctggaatt ggtacctagc ggcaaactgg caaccacaag acgccaacag     780
ctgccccggga atgctaccag ctggacctgg acagatctcg acccgacac  agactatgaa    840
gtatcactgc tgcctgagtc caacgtgcac ctcctgaggc cgcagcacgt gcgagtacgc     900
acactgcaag aggaggccgg gcagaacgc  atcgtcatct cgcatgcgag ccgcgcagc      960
ctccgcgtaa gctgggcccc cgcgcttggc ccggactccg ctctcggcta ccatgtacag    1020
```

-continued

```
ctcggacctc tgcagggcgg gtccctagag cgcgtggagg tgccagcagg ccagaacagc       1080
actaccgtcc agggcctgac gccctgcacc acttacctgg tgactgtgac tgccgccttc       1140
cgctccggcc gccagagggc gctgtcggct aaggcctgta cggcctctgg cgcgcggacc       1200
cgtgctccgc agtccatgcg gccggaggct ggaccgcggg agccctgaac tgcctgcctg       1260
ctcgtc                                                                   1266
```

<210> SEQ ID NO 4
<211> LENGTH: 415
<212> TYPE: PRT
<213> ORGANISM: Mus musculus

<400> SEQUENCE: 4

```
Met Leu Phe Trp Thr Ala Phe Ser Met Ala Leu Ser Leu Arg Leu Ala
 1               5                  10                  15

Leu Ala Arg Ser Ser Ile Glu Arg Gly Ser Thr Ala Ser Asp Pro Gln
            20                  25                  30

Gly Asp Leu Leu Phe Leu Leu Asp Ser Ser Ala Ser Val Ser His Tyr
        35                  40                  45

Glu Phe Ser Arg Val Arg Glu Phe Val Gly Gln Leu Val Ala Thr Met
    50                  55                  60

Ser Phe Gly Pro Gly Ala Leu Arg Ala Ser Leu Val His Val Gly Ser
65                  70                  75                  80

Gln Pro His Thr Glu Phe Thr Phe Asp Gln Tyr Ser Ser Gly Gln Ala
                85                  90                  95

Ile Arg Asp Ala Ile Arg Val Ala Pro Gln Arg Met Gly Asp Thr Asn
            100                 105                 110

Thr Gly Leu Ala Leu Ala Tyr Ala Lys Glu Gln Leu Phe Ala Glu Glu
        115                 120                 125

Ala Gly Ala Arg Pro Gly Val Pro Lys Val Leu Val Trp Val Thr Asp
    130                 135                 140

Gly Gly Ser Ser Asp Pro Val Gly Pro Pro Met Gln Glu Leu Lys Asp
145                 150                 155                 160

Leu Gly Val Thr Ile Phe Ile Val Ser Thr Gly Arg Gly Asn Leu Leu
                165                 170                 175

Glu Leu Leu Ala Ala Ala Ser Ala Pro Ala Glu Lys His Leu His Phe
            180                 185                 190

Val Asp Val Asp Asp Leu Pro Ile Ile Ala Arg Glu Leu Arg Gly Ser
        195                 200                 205

Ile Thr Asp Ala Met Gln Pro Gln Gln Leu His Ala Ser Glu Val Leu
    210                 215                 220

Ser Ser Gly Phe Arg Leu Ser Trp Pro Pro Leu Thr Ala Asp Ser
225                 230                 235                 240

Gly Tyr Tyr Val Leu Glu Leu Val Pro Ser Gly Lys Leu Ala Thr Thr
                245                 250                 255

Arg Arg Gln Gln Leu Pro Gly Asn Ala Thr Ser Trp Thr Trp Thr Asp
            260                 265                 270

Leu Asp Pro Asp Thr Asp Tyr Glu Val Ser Leu Leu Pro Glu Ser Asn
        275                 280                 285

Val His Leu Leu Arg Pro Gln His Val Arg Val Arg Thr Leu Gln Glu
    290                 295                 300

Glu Ala Gly Pro Glu Arg Ile Val Ile Ser His Ala Arg Pro Arg Ser
305                 310                 315                 320
```

```
Leu Arg Val Ser Trp Ala Pro Ala Leu Gly Pro Asp Ser Ala Leu Gly
                325                 330                 335

Tyr His Val Gln Leu Gly Pro Leu Gln Gly Ser Leu Glu Arg Val
            340                 345                 350

Glu Val Pro Ala Gly Gln Asn Ser Thr Thr Val Gln Gly Leu Thr Pro
            355                 360                 365

Cys Thr Thr Tyr Leu Val Thr Val Ala Ala Phe Arg Ser Gly Arg
370                 375                 380

Gln Arg Ala Leu Ser Ala Lys Ala Cys Thr Ala Ser Gly Ala Arg Thr
385                 390                 395                 400

Arg Ala Pro Gln Ser Met Arg Pro Glu Ala Gly Pro Arg Glu Pro
                405                 410                 415

<210> SEQ ID NO 5
<211> LENGTH: 1254
<212> TYPE: DNA
<213> ORGANISM: Homo sapiens

<400> SEQUENCE: 5
atgctcccct ggacggcgct cggcctggcc ctgagcttgc ggctggcgct ggcgcggagc      60
ggcgcggagc gcggtccacc agcatcagcc cccgagggg  acctgatgtt cctgctggac     120
agctcagcca cgtctctca  ctacgagttc tcccggggttc gggagtttgt ggggcagctg    180
gtggctccac tgcccctggg caccggggcc ctgcgtgcca gtctggtgca cgtgggcagt    240
cggccataca ccgagttccc cttcggccag cacagctcgg gtgaggctgc ccaggatgcg    300
gtgcgtgctt ctgcccagcg catgggtgac acccacactg gcctggcgct ggtctatgcc    360
aaggaacagc tgttttgctga agcatcaggt gcccggccag gggtgcccaa agtgctggtg    420
tgggtgacag atggcggctc cagcgaccct gtgggccccc ccatgcagga gctcaaggac    480
ctgggcgtca ccgtgttcat tgtcagcacc ggccgaggca acttcctgga gctgtcagcc    540
gctgcctcag ccccctgccga gaagcacctg cactttgtgg acgtggatga cctgcacatc    600
attgtccaag agctgagggg ctccattctc gcgatgcggc gcagcagct  ccatgccacg    660 gagatcacgt ccagcggctt ccgcctggcc tggccacccc tgctgaccgc agactcgggc    720
tactatgtgc tggagctggt gcccagcgcc cagccggggg ctgcaagacg ccagcagctg    780
ccagggaacg ccacggactg gatctgggcc ggcctcgacc gggacacgga ctacgacgtg    840
gcgctagtgc ctgagtccaa cgtgcgcctc ctgaggcccc agatcctgcg ggtgcgcacg    900
cggccagagg aggccgggcc agagcgcatc gtcatctccc cgcccggcc  gcgcagcctc    960 cgcgtgagtt gggcccagc  gctgggctca gccgcggcgc tcggctacca cgtgcagttc   1020
gggccgctgc ggggcgggga ggcgcagcgg gtggaggtgc ccgcgggccg caactgcacc   1080
acgctgcagg gcctggcgcc gggcaccgcc tacctggtga ccgtgaccgc cgccttccgc   1140
tcgggccgcg agagcgcgct gtccgccaag gcctgcacgc ccgacggccc cgcccgcgc   1200 ccacgccccg tgcccgcgc  cccgaccccg ggaccgcca  gccgtgagcc gtaa         1254

<210> SEQ ID NO 6
<211> LENGTH: 418
<212> TYPE: PRT
<213> ORGANISM: Homo sapiens

<400> SEQUENCE: 6

Met Leu Pro Trp Thr Ala Leu Gly Leu Ala Leu Ser Leu Arg Leu Ala
1               5                   10                  15
```

-continued

```
Leu Ala Arg Ser Gly Ala Glu Arg Gly Pro Pro Ala Ser Ala Pro Arg
         20                  25                  30

Gly Asp Leu Met Phe Leu Leu Asp Ser Ser Ala Ser Val Ser His Tyr
     35                  40                  45

Glu Phe Ser Arg Val Arg Glu Phe Val Gly Gln Leu Val Ala Pro Leu
 50                  55                  60

Pro Leu Gly Thr Gly Ala Leu Arg Ala Ser Leu Val His Val Gly Ser
 65                  70                  75                  80

Arg Pro Tyr Thr Glu Phe Pro Phe Gly Gln His Ser Ser Gly Glu Ala
                 85                  90                  95

Ala Gln Asp Ala Val Arg Ala Ser Ala Gln Arg Met Gly Asp Thr His
            100                 105                 110

Thr Gly Leu Ala Leu Val Tyr Ala Lys Glu Gln Leu Phe Ala Glu Ala
        115                 120                 125

Ser Gly Ala Arg Pro Gly Val Pro Lys Val Leu Val Trp Val Thr Asp
130                 135                 140

Gly Gly Ser Ser Asp Pro Val Gly Pro Pro Met Gln Glu Leu Lys Asp
145                 150                 155                 160

Leu Gly Val Thr Val Phe Ile Val Ser Thr Gly Arg Gly Asn Phe Leu
                165                 170                 175

Glu Leu Ser Ala Ala Ser Ala Pro Ala Glu Lys His Leu His Phe
            180                 185                 190

Val Asp Val Asp Asp Leu His Ile Ile Val Gln Glu Leu Arg Gly Ser
        195                 200                 205

Ile Leu Asp Ala Met Arg Pro Gln Gln Leu His Ala Thr Glu Ile Thr
    210                 215                 220

Ser Ser Gly Phe Arg Leu Ala Trp Pro Leu Leu Thr Ala Asp Ser
225                 230                 235                 240

Gly Tyr Tyr Val Leu Glu Leu Val Pro Ser Ala Gln Pro Gly Ala Ala
                245                 250                 255

Arg Arg Gln Gln Leu Pro Gly Asn Ala Thr Asp Trp Ile Trp Ala Gly
            260                 265                 270

Leu Asp Pro Asp Thr Asp Tyr Asp Val Ala Leu Val Pro Glu Ser Asn
        275                 280                 285

Val Arg Leu Leu Arg Pro Gln Ile Leu Arg Val Arg Thr Arg Pro Glu
    290                 295                 300

Glu Ala Gly Pro Glu Arg Ile Val Ile Ser His Ala Arg Pro Arg Ser
305                 310                 315                 320

Leu Arg Val Ser Trp Ala Pro Ala Leu Gly Ser Ala Ala Ala Leu Gly
                325                 330                 335

Tyr His Val Gln Phe Gly Pro Leu Arg Gly Gly Glu Ala Gln Arg Val
            340                 345                 350

Glu Val Pro Ala Gly Arg Asn Cys Thr Thr Leu Gln Gly Leu Ala Pro
        355                 360                 365

Gly Thr Ala Tyr Leu Val Thr Val Thr Ala Ala Phe Arg Ser Gly Arg
    370                 375                 380

Glu Ser Ala Leu Ser Ala Lys Ala Cys Thr Pro Asp Gly Pro Arg Pro
385                 390                 395                 400

Arg Pro Arg Pro Val Pro Arg Ala Pro Thr Pro Gly Thr Ala Ser Arg
                405                 410                 415

Glu Pro
```

<210> SEQ ID NO 7

<211> LENGTH: 539
<212> TYPE: DNA
<213> ORGANISM: Mus musculus

<400> SEQUENCE: 7

```
agggggacct gttgttcctg ttggacagct cagccagcgt gtcacactat gagttctcaa    60
gagttcggga atttgtgggg cagctggtgg ctacgatgtc tttcggaccc ggggctctgc   120
gtgctagtct ggtgcacgtg ggcagccagc ctcacacaga gtttactttt gaccagtaca   180
gttcaggcca ggctatacgg gatgccatcc gtgttgcacc ccaacgtatg ggtgatacca   240
acacaggcct ggcactggct tatgccaaag aacaattgtt tgctgaggaa gcaggtgccc   300
ggccaggggt tcccaaggtg ctggtgtggg tgacagatgg tggctccagc gaccccgtgg   360
gccccctat gcaggagctc aaggacctgg gtgtcaccat cttcattgtc agcactggcc   420
gaggcaacct gttggagctg ttggcagctg cctcggctcc tgccgagaag cacctacact   480
tgtggatgt ggatgatctt cctatcattg cccgggagct gcggggctcc ataactgat   539
```

<210> SEQ ID NO 8
<211> LENGTH: 180
<212> TYPE: PRT
<213> ORGANISM: Mus musculus

<400> SEQUENCE: 8

```
Gln Gly Asp Leu Leu Phe Leu Leu Asp Ser Ser Ala Ser Val Ser His
  1               5                  10                  15
Tyr Glu Phe Ser Arg Val Arg Glu Phe Val Gly Gln Leu Val Ala Thr
             20                  25                  30
Met Ser Phe Gly Pro Gly Ala Leu Arg Ala Ser Leu Val His Val Gly
         35                  40                  45
Ser Gln Pro His Thr Glu Phe Thr Phe Asp Gln Tyr Ser Ser Gly Gln
     50                  55                  60
Ala Ile Arg Asp Ala Ile Arg Val Ala Pro Gln Arg Met Gly Asp Thr
 65                  70                  75                  80
Asn Thr Gly Leu Ala Leu Ala Tyr Ala Lys Glu Gln Leu Phe Ala Glu
                 85                  90                  95
Glu Ala Gly Ala Arg Pro Gly Val Pro Lys Val Leu Val Trp Val Thr
            100                 105                 110
Asp Gly Gly Ser Ser Asp Pro Val Gly Pro Pro Met Gln Glu Leu Lys
        115                 120                 125
Asp Leu Gly Val Thr Ile Phe Ile Val Ser Thr Gly Arg Gly Asn Leu
    130                 135                 140
Leu Glu Leu Leu Ala Ala Ala Ser Ala Pro Ala Glu Lys His Leu His
145                 150                 155                 160
Phe Val Asp Val Asp Asp Leu Pro Ile Ile Ala Arg Glu Leu Arg Gly
                165                 170                 175
Ser Ile Thr Asp
            180
```

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 9

```
ctcaaagcca tgcgtagtcc                                                 20
```

-continued

```
<210> SEQ ID NO 10
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 10
agaacgcatc gtcatctcgc                                                   20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 11
agaacgcatc gtcatctcgc                                                   20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 12
tcaagggcat atccaacaac                                                   20

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 13
ctggtcatcg ccgcccttgc                                                   20

<210> SEQ ID NO 14
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 14
gaccagcgtt aattcctttc gt                                                22

<210> SEQ ID NO 15
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 15
ccgggtttcc cggaagt                                                      17

<210> SEQ ID NO 16
<211> LENGTH: 32
<212> TYPE: DNA
<213> ORGANISM: Artificial Sequence
<220> FEATURE:
```

<223> OTHER INFORMATION: Oligonucleotide primer

<400> SEQUENCE: 16
ttactggcaa catcaacagg actcctcgta tt                                    32

<210> SEQ ID NO 17
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 17
ccacaggact agaacacctg ctaa                                             24

<210> SEQ ID NO 18
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 18
cctaagatga gcgcaagttg aa                                               22

<210> SEQ ID NO 19
<211> LENGTH: 9060
<212> TYPE: DNA
<213> ORGANISM: Homo sapiens

<400> SEQUENCE: 19
cctctgcatt ccagccacct gccctgggcc cagctccaaa ggaaggggc ccaagctctc       60 tgaataaaag gtgcacatga ggaccaagga ggcctgacac tgggagggga cagctccacc    120
tcctctcccc ggacacccca aaaggcgag acgttcacaa gctgtcctgt cggcggctgc     180
tgtttgtgga ggagtaaagc atcctagcga gactgcaggc tcggtgtaca tctgatttac    240
tgaattttaa agtctgggat gttagtgggg aagaggcgag gtgagcattg cgtgacgccg    300
aggactaggc ggggcgggga ctgcacctgg ctaggcaccc ccaccctggg caacttgccc    360
acggacccca gggcagtgag tagtgacagg aggtagcccg gggtgagacc tctcacagca    420
agaagatggt gtggttgctg gggcctccct ggagagtgtc gtccctgcgg ccctgggaa     480 gtgctccctc acgacggaag gtttcctgtc agtgcggtcc cggggcctga tagtggcggt    540
gggcgggtgg ggtcacgtgt cctcaaggtc ctgaatgccc agctctgccc cattcctctg    600
attcccagtg gctgctagct ggacccagct ggtgtcctgg gcatgaaggc agggccaccg    660
tccccagcag gtgctgccct cctggccagc tgagcatcct ggccaccatc agcgtccagg    720 tgccctact cgcccttcct cttcttcaga agcctttgcg gacctgacct gggccagctt    780
cccgcgattc cccttccgct tcctatcaac gtccaggacc caagctgccc gccccaggcc    840
agcccttgcc acttggggcc cggtcttcac acgtgggagt ctgaccgggg ctcctccctg    900
aacagtcctg ggtctgacgc tctcaattat caccacgga cccacacgac gcccggctct    960
gggcggggat ggggccgggg ctgctgcggg gtcccgccag gcgaggcccc agccctggag   1020
ggcaggcgcc aggcggggaa gccctgcggc cgcaggagga gggccgggt cgcgcggagt    1080 ccgcgtgggg aaaggccggg cctgcacccg tctgccgggt gggcgcctc cgctccgggt   1140 tcgggacaca ggggccctca gtaggcgcc ggccctctcg gctgggcggg gacgccggct   1200
tacggctcac ggctggcggt cccgggggtc ggggcgcggg gcacggggcg tgggcgcggg   1260

```
cgcgggccgt cgggcgtgca ggccttggcg gacagcgcgc tctcgcgccc cgagcggaag    1320
gcggcggtca cggtcaccag gtaggcggtg cccggcgcca ggccctgcag cgtggtgcag    1380
ttgcggcccg cgggcacctc cacccgctgc gcctccccgc cccgcagcgg cccgaactgc    1440
acgtggtagc cgagcgccgc ggctgagccc agcgctgggg cccaactcac gcggaggctg    1500
cgcggccggg cgtgggagat gacgatgcgc tctggcccgg cctcctctgg ggcggggagg    1560
gcggcgagct gcgtggggc cggcccagcc cccgactccg ggcccgaagc ccccggccct    1620
gcctcaccgg gccgcgtgcg cacccgcagg atctggggcc tcaggaggcg cacgttggac    1680
tcaggcacta gcgccacgtc gtagtccgtg tccgggtcga ggccggccca gatccagtcc    1740
gtggcgttcc ctggcagctg ctggcgtctt gcagccccg gctgggcgct gggcaccagc    1800
tccagcacat agtagcccga gtctgcggtc agcagggtg gccaggccag gcggaagccg    1860
ctggacgtga tctccgtggc atggagctgc tgccgccgca tcgcgtctgt gggtggtgca    1920 ggggtcagg gaacagcggt cagttcctcc tccgctgctg gagggcggcc ctggctgatg    1980
gggaagatct ggagattgga ggccccacta ggaaagacgg ggccccgcgg ccaaggagct    2040
gctggagcca tgccccgcag atgctgggga ttctcagaac gtgccttggc tgggggagga    2100
cggaggaaag ggtgcagccc cctcaggccc tgtcagaagc gccctgcct cccttagccc    2160 caaacccagt cctttgtgga gaggtgcagt ggccagatca gtgaccagga caaaggtcct    2220
caaagacggc agagtccacg gtggtgcctg agagcagagg accagcccca gcctgagtgg    2280
ccaggccggg gtctgaggtc agcccggctc tctgagctgc agctaggaga tgggagacca    2340
caggggcagg ccctgggtt ctggaggcgc tgcctgccct gggtcccag gagagtgtgg     2400 ggtggggttc tccagagggg gactcctgga cctgtgacac caagcccac atagccctct    2460 gagtgaccct gctgtggcga ggctcataaa tgtctgcgct gggttaaagc tatcaggatc    2520
ttcctcctgc agtgctgggt gcctgggcca ctttcttccc atccccacc ctcagacccg    2580 gcctctttcc caggagcccc caccctgctg cctggcccct cggcactgca gcctcaggct    2640
tttcctttgg ctgcttaagg cagcctttcc tcctggtccc ctccaggcgc agctgcactg    2700
ggtgacctgg ggccactagg ggccagacgt ccctggggaa accttgggga gggccgtcca    2760
cccctctcca acccacagtc caaccccttc cggctctggg tggatgatta acccacagac    2820
ggagacttgg tgagatcccc agggttggca tttttcagtg gctgcagcag gctgagccag    2880
tggccggttc ctcatctcca gccccagctc cttcagggct tggctgggc agggaggtcc     2940 agaaaaaaag ccaatgggag ctgctcagct cctgcctcag gccttccctg gtccggcctc    3000
tcaggaaacc ctcacagtgg gcctgcagtc cgaactagtt caaagccctc ggcggctgtc    3060
cccacccagg agaggtgccc tgtgctctct gggggggcag tccctgacct ttctggctca    3120
cccctctcca ggtatggtgg gcatgctcag gagcacatgc tgcccatctg cagagtcccc    3180
agacttggaa gcttcttcct gggcctacac ccgggctctg cactccctgg ggcctcgagg    3240
tctgggctgg acacatcagc agggagctac acctggaggt ggctactcaa gcctgccccc    3300
gtctcagcag ggtacacggg tcgcccagtg aagagtgtgc atagacaagc tgcatcactc    3360
agccctgcac cctaggggta ccacagcccc ggaggccctg gccgctgctc tggggacatg    3420
agatcttccc aaagtctcaa cccagcctct ccttctgcgg ctcccagcta gggctccctg    3480
ggccctgcct cctcccgcat accgagaatg gagcccctca gctcttggac aatgatgtgc    3540
aggtcatcca cgtccacaaa gtgcaggtgc ttctcggcag gggctgaggc agcggctgac    3600
```

```
agctccagga agttgcctcg gccggtgctg acaatgaaca cggtgacgcc caggtccttg   3660
agctcctgca tgggggggcc cacagggtcg ctggagccgc catctgtcac ccacaccagc   3720
actttgggca cccctggccg ggcacctgat gcttcagcaa acagctgttc cttggcatag   3780
accagcgcca ggccagtgtg ggtgtcaccc atgcgctggg cagaagcacg caccgcatcc   3840
tgggcagcct cacccgagct gtgctggccg aaggggaact cggtgtatgg ccgactgccc   3900
acgtgcacca gactggcacg cagggccccg gtgcccaggg gcagtggagc caccagctgc   3960
cccacaaact cccgaacccg ggagaactcg tagtgagaga cgctggctga gctgtccagc   4020
aggaacatca ggtcccctcg gggggctgat gctggtggac ctggggggaaa ggaggaatgc   4080 tcagcctcag gtgtgggccc ccagacagc cccacagcaa ggcagggtcc cccagggccc   4140
cagctttcct taagtggatg cttgccttct cccaaaggtc ctaggttggg ggaaagagga   4200
actctaagca agaggcctgt acttttgggg gtttcactgc acactggcca tgggatctag   4260
ggctctctct gggcttgtgt tatcccatct gtgagagggc gactctccgc tccaagcccc   4320
cacaccttcc cattcctcac agaccctgca agcaggtgga gccaagagtc ctggcctagg   4380
cccccaggac aggcctgagc cgtggggctg ttccctccag gcatggcttt cagaggagca   4440
gcctgaggct ggagttcagc cacgcagctc agcctgcagg tgaggcaccc tgggcatgca   4500
cacagcagca ggggaaggtg tcggaggcac agcaatgacc acgccggatg gcctggctgg   4560
agcccagacc ccgcttacta gatggtggcc cctccctgg cctccatcct ccagcccacc   4620
tggactcaca caacaagata taaccccccag cagcctgaaa gccggaacag cccctcgcag   4680
gcttccccct tcctccgggc acctccgggg tggaggctga tgcccctac accgcccctc   4740 cccaccaagc cagggcacca gcgtgcctca attctagtcc cggccttgcg gttttcccca   4800
gtgcggtggg gcgactccaa cttccctacc atccctccac taagggccct cgcaagggta   4860
gggaaactga ggcaggggtg ccccccttgac agacatctcc ctcttcctgt ccaggcccgc   4920
gatcccgcag agatgcgggc cgggacggcc cctatgcccc ggcgctcacg gacggtgtcg   4980
cctggagcac ctgggccgcc agcctcaggt gagcaggacg ctccgcccgc gccccgcccc   5040
ggctcccgca gcctcccagc ccgcccgccc gtccggagca ggggacagcg acggccttgc   5100
gcgggcagcg gcgcagagcg gtcaccagaa gccccagccc cggccggcc gcccgccgca   5160 ctcaccgcgc tccgcgccgc tccgcgccag cgccagccgc aagctcaggg ccaggccgag   5220
cgccgtccag gggagcatcg cgcgcgaggg acggggcgcg ctcggcaact cgctcgctcg   5280
ctcgctcgct cggggctgca gggcgcgtca ccgcgcggac caggccggcc ccgccccgg   5340 gaggcccctc cccgagcggc cacacccacg ccgaggccac gcccacgccc tccggcgcga   5400
gcggagggcc acgcgcacag accccggaga ggcgcgcacg agcggacccc gacacgcagg   5460
gacacgcagc accagccgag atacgaccga ggcacgcacg cgcaggcacg cacacacaca   5520
cactccagtc tccctctccc ggccgaggct gtgcggccca cgctctccac ccctctccga   5580
cccccagccg cgggagccga gcagggaggt accaggctag gccctccccca tgcccaccac   5640 tgccgtgact ctgggtgctg ggtcccagc agcaggccc aagagaaccc caggggctgg   5700
cggtggcacc aaaaaaacac gtccagaccg tggtttcgcc ttggcctccg cgctggaggc   5760
ggataggtgt ctggagtaac aggacatgta tcccaggac tgaccagcag ggatgggaag   5820
gaccatgggg tggaacttac aaggacacag tggcttgaaa ggggacagaa gacaggaatt   5880
cgagagagac tcgaagcacc cacgccacct gggcttcttg gaggaagagg catgggagtg   5940
ggagatggtt ggttgaggcc ctgtccagtg ggaccacact gggcctgtta cccatatacc   6000
```

```
ctacccagtg aggggcccag actccaggac ccaggacaca cccccagcag gactggaggg    6060
tcccactggt gagacaggag ctcttgagtc ttggggtctt ggtgaggccc agacgagagg    6120
tggctggttg caggggcgt  cctgagggac agtggctccc agggcagatt tcccctgctt    6180
gggtggggct gggccagcag tgtcccctgg acaggagaac cctaccccgg ccctccctcg    6240
gagtagccat ggccctcttc cagggcctcc tcagctcaga gctgggaggt ggggacgtg    6300
gggggtgtc  tgccaggatg tctcctcctt ccccacccctc tcctggagga tgcgccgcgg    6360
gagaacggat ggggctccac aggcttcctt cctccctttc aggcaggtga cacaccgcgg    6420
ggccgtgcgg acggccagca ctcgactttg cctaaaaaag gaagcagcag gctgaggctg    6480
aggagctggc ggcaggaaca agggagagct gtgtccccgc cggcgccccc cacccccct    6540
gccgggatc  ttggcagtgg aggtgctggc tgcgctccac agacctcaga cctcggctgg    6600
gaccagaaat gcctggtgct tccgcctggg cccggtgggg ggactttggg tcccagagt    6660
gcaagctgta ccacttcgag gggcctcgcc aggccccccca gccccagta cacaggggct    6720
gccgtgagaa tgacgctgaa ggccgcagcc gctggaggac ctggggtctg accgaaagct    6780
ggctgcagac cctgcggagg cacgtccagg tagtcaggca gggagctggg ccgagggtcc    6840
cccaccctgg ggaggctcac agccagtggc ccgcttgtcc cccacccctcg cccagcaggc    6900
gggccacagt cacacctcag ccagccttgc agggctgacg ggaagttttc cctcacttct    6960
ggaaaaagtg agcgggtctt cttggctgtg actcaggccc tcaaggaagc ggccgccctc    7020
ctcccttcag ctcgccatca gcgggagaag gcacaggagg cctggcctcc acccagcctg    7080
ggccgagctc agccacctgc cttgctcccg gctctgcctg gagtccctcc agctaggaga    7140
ccctccccat cagctctccc cgtgcccctc agtcttcagg actcattctt gtgtcctgcc    7200
ctccccccgc tgtctccacc ccggaggagg gacgtggaca gagggtccca gagagcatgg    7260
ggtcagccag aggtgcagtg tcagggcccg gccggacttt gaggcagaca ccggaggaag    7320
cacaaatata acagccggaa ccctccactc tccagggaga agggcccggg gtaagaggca    7380
gaggcaagga cgggtcaggc cagatcacag tgggtgctgg ccccgagccc tctgcctcct    7440
gcaggcacag cccctgtctg atcctggtgg cctggggccc catgggtggg ggagcagcct    7500
ggtttggctg cggccacccc gccccacgg  tctgggcctg ggctgtggga gtccctgtgc    7560
ctcacttccc ggagccagcc tgccctgccg gtctgtctgc aggcaggtgg agagagttcc    7620
aggaagctgg ggaggctgct gtcacccggg caccgcccct gccccaccc  gcctttgga    7680
atgctccctc ctccgcacaa tccaggcttc tgcagaagat gaagggcctt ttgtccccag    7740
ctggctgtgg tcatgtttga ccctgggtaa aagggcaact cctgaggcct ctgaccccac    7800
ccctgacccg agctgagggc aggacgccca ggcccgcacc cggcgccttt tgttgctgtt    7860
ttcacgtatc tcacaaacgt actcaagcac acacaggagc agatggacgg ggcggtgagg    7920
ggcagcagtg gtgagggca  gcggcggtga ggggcagcgg cggtgagggg cagcggtgcg    7980
ggcctgaggc actgctctgg ggtgtgcctg agcccacccc acaacagtaa gtggggcaga    8040
gcagggtca  ccaagagagc agggcccacg cagctcctag actcaacctg ctcactgggg    8100
tcaaggacag gtcttggggg cctcgggggt cacttttcac ttcccaggag cccaggcctg    8160
cccctctggc cccagagctg accccccctca gtccccgtg  ccagcagcag ctgggtggc    8220
gggtagacac ctggcgggta gcagcctggg taggggtggg agctgcacca tctgcgtctg    8280
tccatccatc cctcgtctgt gtgctgggca cagccgcgcc ccagcctcag tgctggggac    8340
```

-continued

```
acacaggcgc cgggccagca ctgccaggct aggagggtgg gcggtgaaca gctaggaaag    8400
atacggtcta cttgttttcc ctgtgagaac aggggggtcac tggggactcg cacgcaaggg    8460
gtacccgagg aagagccttc caggcagaga aaggaaccg cgagtgctga gagcagggtg     8520
gggtgggcag gaggggcctg cgccaggact gcaggggcag agcaggctgg gggccttcgg    8580
gaggggtggc cgggtggagg gtgttgccgg cctcgacagg ggcaggaggt tcgtcacagc    8640
gaggacagag cccggcccgg tgggagccgg agagcagcag gcctgaatga cccagggttt    8700
cctaatagca gggccccttc cttgtgtggg tccctcact ttgcctctct gctgggacat     8760
ccttccctga aagggagagg aggaccacat gctgccctt ccccagacac agtccagaca     8820
ggcccaggcc acagccctgg gcagacgcaa aactcccagg ggcctggact gggataggga    8880
ggaggcagca gggagggact gacctatgtc cacacaccac aagggactcc cagaggcggg    8940
tggggcggag ctgggagcag gggccttagc cctcagacca gcccactcac cctggggagt    9000
tcctgcccca cagcctgccc agcttacagg cctggggggca ggggcaggcc agcacaggcc    9060
```

<210> SEQ ID NO 20
<211> LENGTH: 418
<212> TYPE: PRT
<213> ORGANISM: Homo sapiens

<400> SEQUENCE: 20

```
Met Leu Pro Trp Thr Ala Leu Gly Leu Ala Leu Ser Leu Arg Leu Ala
1               5                   10                  15

Leu Ala Arg Ser Gly Ala Glu Arg Gly Pro Ala Ser Ala Pro Arg
            20                  25                  30

Gly Asp Leu Met Phe Leu Leu Asp Ser Ser Ala Ser Val Ser His Tyr
        35                  40                  45

Glu Phe Ser Arg Val Arg Glu Phe Val Gly Gln Leu Val Ala Pro Leu
    50                  55                  60

Pro Leu Gly Thr Gly Ala Leu Arg Ala Ser Leu Val His Val Gly Ser
65                  70                  75                  80

Arg Pro Tyr Thr Glu Phe Pro Phe Gly Gln His Ser Ser Gly Glu Ala
                85                  90                  95

Ala Gln Asp Ala Val Arg Ala Ser Ala Gln Arg Met Gly Asp Thr His
            100                 105                 110

Thr Gly Leu Ala Leu Val Tyr Ala Lys Glu Gln Leu Phe Ala Glu Ala
        115                 120                 125

Ser Gly Ala Arg Pro Gly Val Pro Lys Val Leu Val Trp Val Thr Asp
    130                 135                 140

Gly Gly Ser Ser Asp Pro Val Gly Pro Pro Met Gln Glu Leu Lys Asp
145                 150                 155                 160

Leu Gly Val Thr Val Phe Ile Val Ser Thr Gly Arg Gly Asn Phe Leu
                165                 170                 175

Glu Leu Ser Ala Ala Ser Ala Pro Ala Glu Lys His Leu His Phe
            180                 185                 190

Val Asp Val Asp Asp Leu His Ile Ile Val Gln Glu Leu Arg Gly Ser
        195                 200                 205

Ile Leu Asp Ala Met Arg Pro Gln Gln Leu His Ala Thr Glu Ile Thr
    210                 215                 220

Ser Ser Gly Phe Arg Leu Ala Trp Pro Pro Leu Leu Thr Ala Asp Ser
225                 230                 235                 240

Gly Tyr Tyr Val Leu Glu Leu Val Pro Ser Ala Gln Pro Gly Ala Ala
                245                 250                 255
```

-continued

```
Arg Arg Gln Gln Leu Pro Gly Asn Ala Thr Asp Trp Ile Trp Ala Gly
            260                 265                 270

Leu Asp Pro Asp Thr Asp Tyr Asp Val Ala Leu Val Pro Glu Ser Asn
            275                 280                 285

Val Arg Leu Leu Arg Pro Gln Ile Leu Arg Val Arg Thr Arg Pro Glu
            290                 295                 300

Glu Ala Gly Pro Glu Arg Ile Val Ile Ser His Ala Arg Pro Arg Ser
305                 310                 315                 320

Leu Arg Val Ser Trp Ala Pro Ala Leu Gly Ser Ala Ala Leu Gly
            325                 330                 335

Tyr His Val Gln Phe Gly Pro Leu Arg Gly Glu Ala Gln Arg Val
            340                 345                 350

Glu Val Pro Ala Gly Arg Asn Cys Thr Thr Leu Gln Gly Leu Ala Pro
            355                 360                 365

Gly Thr Ala Tyr Leu Val Thr Val Thr Ala Ala Phe Arg Ser Gly Arg
            370                 375                 380

Glu Ser Ala Leu Ser Ala Lys Ala Cys Thr Pro Asp Gly Pro Arg Pro
385                 390                 395                 400

Arg Pro Arg Pro Val Pro Arg Ala Pro Thr Pro Gly Thr Ala Ser Arg
            405                 410                 415

Glu Pro

<210> SEQ ID NO 21
<211> LENGTH: 415
<212> TYPE: PRT
<213> ORGANISM: Mus musculus

<400> SEQUENCE: 21

Met Leu Phe Trp Thr Ala Phe Ser Met Ala Leu Ser Leu Arg Leu Ala
1               5                   10                  15

Leu Ala Arg Ser Ser Ile Glu Arg Gly Ser Thr Ala Ser Asp Pro Gln
            20                  25                  30

Gly Asp Leu Leu Phe Leu Leu Asp Ser Ser Ala Ser Val Ser His Tyr
            35                  40                  45

Glu Phe Ser Arg Val Arg Glu Phe Val Gly Gln Leu Val Ala Thr Met
        50                  55                  60

Ser Phe Gly Pro Gly Ala Leu Arg Ala Ser Leu Val His Val Gly Ser
65                  70                  75                  80

Gln Pro His Thr Glu Phe Thr Phe Asp Gln Tyr Ser Ser Gly Gln Ala
                85                  90                  95

Ile Arg Asp Ala Ile Arg Val Ala Pro Gln Arg Met Gly Asp Thr Asn
            100                 105                 110

Thr Gly Leu Ala Leu Ala Tyr Ala Lys Glu Gln Leu Phe Ala Glu Glu
        115                 120                 125

Ala Gly Ala Arg Pro Gly Val Pro Lys Val Leu Val Trp Val Thr Asp
    130                 135                 140

Gly Gly Ser Ser Asp Pro Val Gly Pro Met Gln Glu Leu Lys Asp
145                 150                 155                 160

Leu Gly Val Thr Ile Phe Ile Val Ser Thr Gly Arg Gly Asn Leu Leu
                165                 170                 175

Glu Leu Leu Ala Ala Ala Ser Ala Pro Ala Glu Lys His Leu His Phe
            180                 185                 190

Val Asp Val Asp Asp Leu Pro Ile Ile Ala Arg Glu Leu Arg Gly Ser
            195                 200                 205
```

```
Ile Thr Asp Ala Met Gln Pro Gln Gln Leu His Ala Ser Glu Val Leu
    210                 215                 220

Ser Ser Gly Phe Arg Leu Ser Trp Pro Pro Leu Leu Thr Ala Asp Ser
225                 230                 235                 240

Gly Tyr Tyr Val Leu Glu Leu Val Pro Ser Gly Lys Leu Ala Thr Thr
                245                 250                 255

Arg Arg Gln Gln Leu Pro Gly Asn Ala Thr Ser Trp Thr Trp Thr Asp
                260                 265                 270

Leu Asp Pro Asp Thr Asp Tyr Glu Val Ser Leu Leu Pro Glu Ser Asn
                275                 280                 285

Val His Leu Leu Arg Pro Gln His Val Arg Val Arg Thr Leu Gln Glu
    290                 295                 300

Glu Ala Gly Pro Glu Arg Ile Val Ile Ser His Ala Arg Pro Arg Ser
305                 310                 315                 320

Leu Arg Val Ser Trp Ala Pro Ala Leu Gly Pro Asp Ser Ala Leu Gly
                325                 330                 335

Tyr His Val Gln Leu Gly Pro Leu Gln Gly Gly Ser Leu Glu Arg Val
                340                 345                 350

Glu Val Pro Ala Gly Gln Asn Ser Thr Thr Val Gln Gly Leu Thr Pro
                355                 360                 365

Cys Thr Thr Tyr Leu Val Thr Val Thr Ala Ala Phe Arg Ser Gly Arg
                370                 375                 380

Gln Arg Ala Leu Ser Ala Lys Ala Cys Thr Ala Ser Gly Ala Arg Thr
385                 390                 395                 400

Arg Ala Pro Gln Ser Met Arg Pro Glu Ala Gly Pro Arg Glu Pro
                405                 410                 415

<210> SEQ ID NO 22
<211> LENGTH: 182
<212> TYPE: PRT
<213> ORGANISM: Artificial Sequence
<220> FEATURE:
<223> OTHER INFORMATION: VA domain from collagen XIV

<400> SEQUENCE: 22

Ile Ala Asp Ile Val Ile Leu Val Asp Gly Ser Trp Ser Ile Gly Arg
1               5                   10                  15

Phe Asn Phe Arg Leu Val Arg Leu Phe Leu Glu Asn Leu Val Ser Ala
                20                  25                  30

Phe Asn Val Gly Ser Glu Lys Thr Arg Val Gly Leu Ala Gln Tyr Ser
            35                  40                  45

Gly Asp Pro Arg Ile Glu Trp His Leu Asn Ala Tyr Gly Thr Lys Asp
        50                  55                  60

Ala Val Leu Asp Ala Val Arg Asn Leu Pro Tyr Lys Gly Gly Asn Thr
65                  70                  75                  80

Leu Thr Gly Leu Ala Leu Thr Tyr Ile Leu Glu Asn Ser Phe Lys Pro
                85                  90                  95

Glu Ala Gly Ala Arg Pro Gly Val Ser Lys Ile Gly Ile Leu Ile Thr
                100                 105                 110

Asp Gly Lys Ser Gln Asp Val Ile Pro Ala Lys Asn Leu Arg
                115                 120                 125

Asp Ala Gly Ile Glu Leu Phe Ala Ile Gly Val Lys Asn Ala Asp Ile
            130                 135                 140

Asn Glu Leu Lys Glu Ile Ala Ser Glu Pro Asp Ser Thr His Val Tyr
145                 150                 155                 160
```

```
Asn Val Ala Asp Phe Asn Phe Met Asn Ser Ile Val Glu Gly Leu Thr
            165                 170                 175

Arg Thr Val Cys Ser Arg
            180

<210> SEQ ID NO 23
<211> LENGTH: 183
<212> TYPE: PRT
<213> ORGANISM: Artificial Sequence
<220> FEATURE:
<223> OTHER INFORMATION: VA domain from collagen VII

<400> SEQUENCE: 23

Ala Ala Asp Ile Val Phe Leu Leu Asp Gly Ser Ser Ile Gly Arg
 1               5                  10                  15

Ser Asn Phe Arg Glu Val Arg Ser Phe Leu Glu Gly Leu Val Leu Pro
                20                  25                  30

Phe Ser Gly Ala Ala Ser Ala Gln Gly Val Arg Phe Ala Thr Val Gln
            35                  40                  45

Tyr Ser Asp Asp Pro Arg Thr Glu Phe Gly Leu Asp Ala Leu Gly Ser
 50                  55                  60

Gly Gly Asp Val Ile Arg Ala Ile Arg Glu Leu Ser Tyr Lys Gly Gly
65                  70                  75                  80

Asn Thr Arg Thr Gly Ala Ala Ile Leu His Val Ala Asp His Val Phe
                85                  90                  95

Leu Pro Gln Leu Ala Arg Pro Gly Val Pro Lys Val Cys Ile Leu Ile
            100                 105                 110

Thr Asp Gly Lys Ser Gln Asp Leu Val Asp Thr Ala Ala Gln Arg Leu
        115                 120                 125

Lys Gly Gln Gly Val Lys Leu Phe Ala Val Gly Ile Lys Asn Ala Asp
    130                 135                 140

Pro Glu Glu Leu Lys Arg Val Ala Ser Gln Pro Thr Ser Asp Phe Phe
145                 150                 155                 160

Phe Phe Val Asn Asp Phe Ser Ile Leu Arg Thr Leu Leu Pro Leu Val
                165                 170                 175

Ser Arg Arg Val Cys Thr Thr
            180

<210> SEQ ID NO 24
<211> LENGTH: 182
<212> TYPE: PRT
<213> ORGANISM: Artificial Sequence
<220> FEATURE:
<223> OTHER INFORMATION: VA domain from collagen XII

<400> SEQUENCE: 24

Lys Ala Asp Ile Val Phe Leu Thr Asp Ala Ser Trp Ser Ile Gly Asp
 1               5                  10                  15

Asp Asn Phe Asn Lys Val Val Lys Phe Ile Phe Asn Thr Val Gly Ala
                20                  25                  30

Phe Asp Glu Val Asn Pro Ala Gly Ile Gln Val Ser Phe Val Gln Tyr
            35                  40                  45

Ser Asp Glu Val Lys Ser Glu Phe Lys Leu Asn Thr Tyr Asn Asp Lys
 50                  55                  60

Ala Leu Ala Leu Gly Ala Leu Gln Asn Ile Arg Tyr Arg Gly Gly Asn
65                  70                  75                  80

Thr Arg Thr Gly Lys Ala Leu Thr Phe Ile Lys Glu Lys Val Leu Thr
```

```
                    85                  90                  95
Trp Glu Ser Gly Met Arg Lys Asn Val Arg Val Leu Gly Val Val Thr
            100                 105                 110

Asp Gly Arg Ser Gln Asp Glu Val Lys Lys Ala Ala Phe Val Ile Gln
        115                 120                 125

Gln Ser Gly Phe Ser Val Phe Val Gly Val Ala Asp Val Asp Tyr
    130                 135                 140

Asn Glu Leu Ala Asn Ile Ala Ser Lys Pro Ser Glu Arg His Val Phe
145                 150                 155                 160

Ile Val Asp Asp Phe Glu Ser Phe Glu Lys Ile Glu Asp Asn Leu Ile
                165                 170                 175

Thr Phe Val Cys Glu Thr
            180

<210> SEQ ID NO 25
<211> LENGTH: 185
<212> TYPE: PRT
<213> ORGANISM: Artificial Sequence
<220> FEATURE:
<223> OTHER INFORMATION: VA domain from collagen VI

<400> SEQUENCE: 25

Ala Ala Asp Ile Val Phe Leu Val Asp Ser Ser Trp Ser Ala Gly Lys
1               5                   10                  15

Asp Arg Phe Leu Leu Val Gln Glu Phe Leu Ser Asp Val Val Glu Ser
            20                  25                  30

Leu Ala Val Gly Asp Asn Asp Phe His Phe Ala Leu Val Arg Leu Asn
        35                  40                  45

Gly Asn Pro His Thr Glu Phe Leu Leu Asn Thr Tyr His Ser Lys Gln
    50                  55                  60

Glu Val Leu Ser His Ile Ala Asn Met Ser Tyr Ile Gly Gly Ser Asn
65                  70                  75                  80

Gln Thr Gly Lys Gly Leu Glu Tyr Val Ile His Ser His Leu Thr Glu
                85                  90                  95

Ala Ser Gly Ser Arg Ala Ala Asp Gly Val Pro Gln Val Ile Val Val
            100                 105                 110

Leu Thr Asp Gly Gln Ser Glu Asp Gly Phe Ala Leu Pro Ser Ala Glu
        115                 120                 125

Leu Lys Ser Ala Asp Val Asn Val Phe Ala Val Gly Val Glu Gly Ala
    130                 135                 140

Asp Glu Arg Ala Leu Gly Glu Val Ala Ser Glu Pro Leu Leu Ser Met
145                 150                 155                 160

His Val Phe Asn Leu Glu Asn Val Thr Ser Leu His Gly Leu Val Gly
                165                 170                 175

Asn Leu Val Ser Cys Ile His Ser Ser
            180                 185

<210> SEQ ID NO 26
<211> LENGTH: 185
<212> TYPE: PRT
<213> ORGANISM: Artificial Sequence
<220> FEATURE:
<223> OTHER INFORMATION: VA domain from matrilin-2

<400> SEQUENCE: 26

Arg Ala Asp Leu Val Phe Ile Ile Asp Ser Ser Arg Ser Val Asn Thr
1               5                   10                  15
```

```
Tyr Asp Tyr Ala Lys Val Lys Glu Phe Ile Leu Asp Ile Leu Gln Phe
            20                  25                  30

Leu Asp Ile Gly Pro Asp Val Thr Arg Val Gly Leu Leu Gln Tyr Gly
        35                  40                  45

Ser Thr Val Lys Asn Glu Phe Ser Leu Lys Thr Phe Lys Arg Lys Ser
 50                  55                  60

Glu Val Glu Arg Ala Val Lys Arg Met Arg His Leu Ser Thr Gly Thr
 65                  70                  75                  80

Met Thr Gly Leu Ala Ile Gln Tyr Ala Leu Asn Ile Ala Phe Ser Glu
                85                  90                  95

Ala Glu Gly Ala Arg Pro Leu Arg Glu Asn Val Pro Arg Ile Ile Met
                100                 105                 110

Ile Val Thr Asp Gly Arg Pro Gln Asp Ser Val Ala Glu Val Ala Ala
            115                 120                 125

Lys Ala Arg Asn Thr Gly Ile Leu Ile Phe Ala Ile Gly Val Gly Gln
130                 135                 140

Val Asp Leu Asn Thr Leu Lys Ala Ile Gly Ser Glu Pro His Lys Asp
145                 150                 155                 160

His Val Phe Leu Val Ala Asn Phe Ser Gln Ile Glu Ser Leu Thr Ser
                165                 170                 175

Val Phe Gln Asn Lys Leu Cys Thr Val
                180                 185
```

<210> SEQ ID NO 27
<211> LENGTH: 184
<212> TYPE: PRT
<213> ORGANISM: Artificial Sequence
<220> FEATURE:
<223> OTHER INFORMATION: VA domain from matrilin-4

<400> SEQUENCE: 27

```
Pro Leu Asp Leu Val Phe Met Ile Asp Ser Ser Arg Ser Val Arg Pro
 1               5                  10                  15

Phe Glu Phe Glu Thr Met Arg Gln Phe Leu Val Gly Leu Leu Arg Ser
                20                  25                  30

Leu Asp Val Gly Leu Asn Ala Thr Arg Val Gly Val Ile Gln Tyr Ser
        35                  40                  45

Ser Gln Val Gln Ser Val Phe Pro Leu Gly Ala Phe Ser Arg Arg Glu
 50                  55                  60

Asp Met Glu Arg Ala Ile Arg Ala Val Val Pro Leu Ala Gln Gly Thr
 65                  70                  75                  80

Met Thr Gly Leu Ala Ile Gln Tyr Ala Met Asn Val Ala Phe Ser Glu
                85                  90                  95

Ala Glu Gly Ala Arg Pro Ser Glu Glu Arg Val Pro Arg Val Leu Val
                100                 105                 110

Ile Val Thr Asp Gly Arg Pro Gln Asp Arg Val Ala Glu Val Ala Ala
            115                 120                 125

Gln Ala Arg Ala Arg Gly Ile Glu Ile Tyr Ala Val Gly Val Gln Arg
130                 135                 140

Ala Asp Val Gly Ser Leu Arg Thr Met Ala Ser Pro Pro Leu Asp Gln
145                 150                 155                 160

His Val Phe Leu Val Glu Ser Phe Asp Ile Gln Glu Phe Gly Leu Gln
                165                 170                 175

Phe Gln Gly Arg Leu Cys Gly Lys
                180
```

```
<210> SEQ ID NO 28
<211> LENGTH: 185
<212> TYPE: PRT
<213> ORGANISM: Artificial Sequence
<220> FEATURE:
<223> OTHER INFORMATION: VA domain from matrilin-3

<400> SEQUENCE: 28

Pro Leu Asp Leu Val Phe Ile Ile Asp Ser Ser Arg Ser Val Arg Pro
 1               5                  10                  15

Leu Glu Phe Thr Lys Val Lys Thr Phe Val Ser Arg Ile Ile Asp Thr
            20                  25                  30

Leu Asp Ile Gly Ala Thr Asp Thr Arg Val Ala Val Val Asn Tyr Ala
        35                  40                  45

Ser Thr Val Lys Ile Glu Phe Gln Leu Asn Thr Tyr Ser Asp Lys Gln
    50                  55                  60

Ala Leu Lys Gln Ala Val Ala Arg Ile Thr Pro Leu Ser Thr Gly Thr
65                  70                  75                  80

Met Ser Gly Leu Ala Ile Gln Thr Ala Met Glu Glu Ala Phe Thr Val
                85                  90                  95

Glu Ala Gly Ala Arg Gly Pro Met Ser Asn Ile Pro Lys Val Ala Ile
            100                 105                 110

Ile Val Thr Asp Gly Arg Pro Gln Asp Gln Val Asn Glu Val Ala Ala
        115                 120                 125

Arg Ala Arg Ala Ser Gly Ile Glu Leu Tyr Ala Val Gly Val Asp Arg
    130                 135                 140

Ala Asp Met Glu Ser Leu Lys Met Met Ala Ser Lys Pro Leu Glu Glu
145                 150                 155                 160

His Val Phe Tyr Val Glu Thr Tyr Gly Val Ile Glu Lys Leu Ser Ala
                165                 170                 175

Arg Phe Gln Glu Thr Pro Cys Ala Leu
            180                 185

<210> SEQ ID NO 29
<211> LENGTH: 185
<212> TYPE: PRT
<213> ORGANISM: Artificial Sequence
<220> FEATURE:
<223> OTHER INFORMATION: VA domain from matrilin-1

<400> SEQUENCE: 29

Pro Thr Asp Leu Val Phe Val Val Asp Ser Ser Arg Ser Val Arg Pro
 1               5                  10                  15

Val Glu Phe Glu Lys Val Lys Val Phe Leu Ser Gln Val Ile Glu Ser
            20                  25                  30

Leu Asp Val Gly Pro Asn Ala Thr Arg Val Gly Leu Val Asn Tyr Ala
        35                  40                  45

Ser Thr Val Lys Pro Glu Phe Pro Leu Arg Ala His Gly Ser Lys Ala
    50                  55                  60

Ser Leu Leu Gln Ala Val Arg Arg Ile Gln Pro Leu Ser Thr Gly Thr
65                  70                  75                  80

Met Thr Gly Leu Ala Leu Gln Phe Ala Ile Thr Lys Ala Leu Ser Asp
                85                  90                  95

Ala Glu Gly Gly Arg Ala Arg Ser Pro Asp Ile Ser Lys Val Val Ile
            100                 105                 110

Val Val Thr Asp Gly Arg Pro Gln Asp Ser Val Arg Asp Val Ser Glu
        115                 120                 125
```

Arg Ala Arg Ala Ser Gly Ile Glu Leu Phe Ala Ile Gly Leu Gly Arg
    130                 135                 140

Val Asp Lys Ala Thr Leu Arg Gln Ile Ala Ser Glu Pro Gln Asp Glu
145                 150                 155                 160

His Val Asp Tyr Val Glu Ser Tyr Asn Val Ile Glu Lys Leu Ala Lys
                165                 170                 175

Lys Phe Gln Glu Ala Phe Cys Val Val
            180                 185

<210> SEQ ID NO 30
<211> LENGTH: 193
<212> TYPE: PRT
<213> ORGANISM: Artificial Sequence
<220> FEATURE:
<223> OTHER INFORMATION: VA domain from VLA

<400> SEQUENCE: 30

Gln Leu Asp Ile Val Ile Val Leu Asp Gly Ser Asn Ser Ile Tyr Pro
1               5                   10                  15

Trp Asp Ser Val Thr Ala Phe Leu Asn Asp Leu Leu Lys Arg Met Asp
            20                  25                  30

Ile Gly Pro Lys Gln Thr Gln Val Gly Ile Val Gln Tyr Gly Glu Asn
        35                  40                  45

Val Thr His Glu Phe Asn Leu Asn Lys Tyr Ser Ser Thr Glu Glu Val
    50                  55                  60

Leu Val Ala Ala Lys Lys Ile Val Gln Arg Gly Gly Arg Gln Thr Met
65                  70                  75                  80

Thr Ala Leu Gly Thr Asp Thr Ala Arg Lys Glu Ala Phe Thr Glu Ala
                85                  90                  95

Arg Gly Ala Arg Arg Gly Val Lys Lys Val Met Val Ile Val Thr Asp
            100                 105                 110

Gly Glu Ser His Asp Asn His Arg Leu Lys Lys Val Ile Gln Asp Cys
        115                 120                 125

Glu Asp Glu Asn Ile Gln Arg Phe Ser Ile Ala Ile Leu Gly Ser Tyr
    130                 135                 140

Asn Arg Gly Asn Leu Ser Thr Glu Lys Phe Val Glu Glu Ile Lys Ser
145                 150                 155                 160

Ile Ala Ser Glu Pro Thr Glu Lys His Phe Phe Asn Val Ser Asp Glu
                165                 170                 175

Leu Ala Leu Val Thr Ile Val Lys Thr Leu Gly Glu Arg Ile Phe Ala
            180                 185                 190

Leu

<210> SEQ ID NO 31
<211> LENGTH: 181
<212> TYPE: PRT
<213> ORGANISM: Artificial Sequence
<220> FEATURE:
<223> OTHER INFORMATION: VA domain from WARP

<400> SEQUENCE: 31

Gln Gly Asp Leu Leu Phe Leu Leu Asp Ser Ser Ala Ser Val Ser His
1               5                   10                  15

Tyr Glu Phe Ser Arg Val Arg Glu Phe Val Gly Gln Leu Val Ala Thr
            20                  25                  30

Met Ser Phe Gly Pro Gly Ala Leu Arg Ala Ser Leu Val His Val Gly
        35                  40                  45

Ser Gln Pro His Thr Glu Phe Thr Phe Asp Gln Tyr Ser Ser Gly Gln
              50                  55                  60

Ala Ile Arg Asp Ala Ile Arg Val Ala Pro Gln Arg Met Gly Asp Thr
 65                  70                  75                  80

Asn Thr Gly Leu Ala Leu Ala Tyr Ala Lys Glu Gln Leu Phe Ala Glu
                     85                  90                  95

Glu Ala Gly Ala Arg Pro Gly Val Pro Lys Val Leu Val Trp Val Thr
                100                 105                 110

Asp Gly Gly Ser Ser Asp Pro Val Gly Pro Pro Met Gln Glu Leu Lys
                115                 120                 125

Asp Leu Gly Val Thr Ile Phe Ile Val Ser Thr Gly Arg Gly Asn Leu
130                 135                 140

Leu Glu Leu Leu Ala Ala Ser Ala Pro Ala Glu Lys His Leu His
145                 150                 155                 160

Phe Val Asp Val Asp Asp Leu Pro Ile Ile Ala Arg Glu Leu Arg Gly
                165                 170                 175

Ser Ile Thr Asp Ala
            180

<210> SEQ ID NO 32
<211> LENGTH: 184
<212> TYPE: PRT
<213> ORGANISM: Artificial Sequence
<220> FEATURE:
<223> OTHER INFORMATION: VA domain from cochlin

<400> SEQUENCE: 32

Lys Ala Asp Ile Ala Phe Leu Ile Asp Gly Ser Tyr Asn Ile Gly Gln
 1               5                  10                  15

Arg Arg Phe Asn Leu Gln Lys Asn Phe Val Gly Lys Val Ala Val Met
                20                  25                  30

Leu Gly Ile Gly Thr Glu Gly Pro His Val Gly Val Val Gln Ala Ser
             35                  40                  45

Glu His Pro Lys Ile Glu Phe Tyr Leu Lys Asn Phe Thr Ala Ala Lys
 50                  55                  60

Glu Val Leu Phe Ala Ile Lys Glu Leu Gly Phe Arg Gly Gly Asn Ser
 65                  70                  75                  80

Asn Thr Gly Lys Ala Leu Lys His Ala Ala Gln Lys Phe Phe Ser Met
                 85                  90                  95

Glu Asn Gly Ala Arg Lys Gly Ile Pro Lys Ile Ile Val Val Phe Leu
                100                 105                 110

Asp Gly Trp Pro Ser Asp Asp Leu Glu Glu Ala Gly Ile Val Ala Arg
                115                 120                 125

Glu Phe Gly Val Asn Val Phe Ile Val Ser Ser Val Ala Lys Pro Thr
130                 135                 140

Thr Glu Glu Leu Gly Met Val Gln Asp Ile Gly Phe Ile Asp Lys Ala
145                 150                 155                 160

Val Cys Arg Asn Asn Gly Phe Phe Ser Tyr Gln Met Pro Ser Trp Phe
                165                 170                 175

Gly Thr Thr Lys Tyr Val Lys Pro
                180

<210> SEQ ID NO 33
<211> LENGTH: 186
<212> TYPE: PRT
<213> ORGANISM: Artificial Sequence
<220> FEATURE:
<223> OTHER INFORMATION: VA domain from vwf

<400> SEQUENCE: 33

Leu Leu Asp Leu Val Phe Leu Leu Asp Gly Ser Ser Arg Leu Ser Glu
1               5                   10                  15

Ala Glu Phe Glu Val Leu Lys Ala Phe Val Val Asp Met Met Glu Arg
            20                  25                  30

Leu Arg Ile Ser Gln Lys Trp Val Arg Val Ala Val Val Glu Tyr His
        35                  40                  45

Asp Gly Ser His Ala Tyr Ile Gly Leu Lys Asp Arg Lys Arg Pro Ser
    50                  55                  60

Glu Leu Arg Arg Ile Ala Ser Gln Val Lys Tyr Ala Gly Ser Gln Val
65                  70                  75                  80

Ala Ser Thr Ser Glu Val Leu Lys Tyr Thr Leu Phe Gln Ile Phe Ser
                85                  90                  95

Lys Ile Asp Arg Pro Glu Ala Ser Arg Ile Ala Leu Leu Leu Met Ala
            100                 105                 110

Ser Gln Glu Pro Gln Arg Met Ser Arg Asn Phe Val Arg Tyr Val Gln
        115                 120                 125

Gly Leu Lys Lys Lys Val Ile Val Ile Pro Val Gly Ile Gly Pro
    130                 135                 140

His Ala Asn Leu Lys Gln Ile Arg Leu Ile Glu Lys Gln Ala Pro Glu
145                 150                 155                 160

Asn Lys Ala Phe Val Leu Ser Ser Val Asp Glu Leu Glu Gln Gln Arg
                165                 170                 175

Asp Glu Ile Val Ser Tyr Leu Cys Asp Leu
            180                 185

<210> SEQ ID NO 34
<211> LENGTH: 85
<212> TYPE: PRT
<213> ORGANISM: Artificial Sequence
<220> FEATURE:
<223> OTHER INFORMATION: F3-3 repeats from collagen XII

<400> SEQUENCE: 34

Pro Arg Asn Leu Lys Val Thr Asp Glu Thr Thr Asp Ser Phe Lys Ile
1               5                   10                  15

Thr Trp Thr Gln Ala Pro Gly Arg Val Leu Arg Tyr Arg Ile Ile Tyr
            20                  25                  30

Arg Pro Val Ala Gly Gly Glu Ser Arg Glu Val Thr Pro Pro Asn
        35                  40                  45

Gln Arg Arg Arg Thr Leu Glu Asn Leu Ile Pro Asp Thr Lys Tyr Glu
    50                  55                  60

Val Ser Val Ile Pro Glu Tyr Phe Ser Gly Pro Gly Thr Pro Leu Thr
65                  70                  75                  80

Gly Asn Ala Ala Thr
            85

<210> SEQ ID NO 35
<211> LENGTH: 86
<212> TYPE: PRT
<213> ORGANISM: Artificial Sequence
<220> FEATURE:
<223> OTHER INFORMATION: F3-12 repeats from fibronectin

<400> SEQUENCE: 35

```
Pro Ser Gln Met Gln Val Thr Asp Val Gln Asp Asn Ser Ile Ser Val
 1               5                  10                  15

Arg Trp Leu Pro Ser Thr Ser Pro Val Thr Gly Tyr Arg Val Thr Thr
                20                  25                  30

Thr Pro Lys Asn Gly Leu Gly Pro Ser Lys Thr Lys Thr Ala Ser Pro
            35                  40                  45

Asp Gln Thr Glu Met Thr Ile Glu Gly Leu Gln Pro Thr Val Glu Tyr
        50                  55                  60

Val Val Ser Val Tyr Ala Gln Asn Arg Asn Gly Glu Ser Gln Pro Leu
65                  70                  75                  80

Val Gln Thr Ala Val Thr
                85

<210> SEQ ID NO 36
<211> LENGTH: 87
<212> TYPE: PRT
<213> ORGANISM: Artificial Sequence
<220> FEATURE:
<223> OTHER INFORMATION: F3-2 repeats from WARP

<400> SEQUENCE: 36

Pro Glu Arg Ile Val Ile Ser His Ala Arg Pro Arg Ser Leu Arg Val
 1               5                  10                  15

Ser Trp Ala Pro Ala Leu Gly Pro Asp Ser Ala Leu Gly Tyr His Val
                20                  25                  30

Gln Leu Gly Pro Leu Gln Gly Gly Ser Leu Glu Arg Val Glu Val Pro
            35                  40                  45

Ala Gly Gln Asn Ser Thr Thr Val Gln Gly Leu Thr Pro Cys Thr Thr
        50                  55                  60

Tyr Leu Val Thr Val Thr Ala Ala Phe Arg Ser Gly Arg Gln Arg Ala
65                  70                  75                  80

Leu Ser Ala Lys Ala Cys Thr
                85

<210> SEQ ID NO 37
<211> LENGTH: 88
<212> TYPE: PRT
<213> ORGANISM: Artificial Sequence
<220> FEATURE:
<223> OTHER INFORMATION: F3-3 repeats from beta-4 integrin

<400> SEQUENCE: 37

Pro Thr Arg Leu Val Phe Ser Ala Leu Gly Pro Thr Ser Leu Arg Val
 1               5                  10                  15

Ser Trp Gln Glu Pro Arg Cys Glu Arg Pro Leu Gln Gly Tyr Ser Val
                20                  25                  30

Glu Tyr Gln Leu Leu Asn Gly Gly Glu Leu His Arg Leu Asn Ile Pro
            35                  40                  45

Asn Pro Ala Gln Thr Ser Val Val Val Glu Asp Leu Leu Pro Asn His
        50                  55                  60

Ser Tyr Val Phe Arg Val Arg Ala Gln Ser Gln Glu Gly Trp Gly Arg
65                  70                  75                  80

Glu Arg Glu Gly Val Ile Thr Ile
                85

<210> SEQ ID NO 38
<211> LENGTH: 85
<212> TYPE: PRT
<213> ORGANISM: Artificial Sequence
```

```
<220> FEATURE:
<223> OTHER INFORMATION: F3-5 repeat from collagen XIV

<400> SEQUENCE: 38

Pro Gln His Leu Glu Val Asp Glu Ala Ser Thr Asp Ser Phe Arg Val
 1               5                  10                  15

Ser Trp Lys Pro Thr Ser Ser Asp Ile Ala Phe Tyr Arg Leu Ala Trp
                20                  25                  30

Ile Pro Leu Asp Gly Gly Glu Ser Glu Val Val Leu Ser Gly Asp
            35                  40                  45

Ala Asp Ser Tyr Val Ile Glu Gly Leu Leu Pro Asn Thr Glu Tyr Glu
 50                  55                  60

Val Ser Leu Leu Ala Val Phe Asp Asp Glu Thr Glu Ser Glu Val Val
65                   70                  75                  80

Ala Val Leu Gly Ala
                85

<210> SEQ ID NO 39
<211> LENGTH: 85
<212> TYPE: PRT
<213> ORGANISM: Artificial Sequence
<220> FEATURE:
<223> OTHER INFORMATION: F3-7 repeat from tenascin-R

<400> SEQUENCE: 39

Pro Lys Asp Ile Thr Ile Ser Asn Val Thr Lys Asp Ser Val Met Val
 1               5                  10                  15

Ser Trp Ser Pro Pro Val Ala Ser Phe Asp Tyr Tyr Arg Val Ser Tyr
                20                  25                  30

Arg Pro Thr Gln Val Gly Arg Leu Asp Ser Ser Val Val Pro Asn Thr
            35                  40                  45

Val Thr Glu Phe Thr Ile Thr Arg Leu Asn Pro Ala Thr Glu Tyr Glu
 50                  55                  60

Ile Ser Leu Asn Ser Val Arg Gly Arg Glu Glu Ser Glu Arg Ile Cys
65                   70                  75                  80

Thr Leu Val His Thr
                85

<210> SEQ ID NO 40
<211> LENGTH: 87
<212> TYPE: PRT
<213> ORGANISM: Artificial Sequence
<220> FEATURE:
<223> OTHER INFORMATION: F3-1 repeat from WARP

<400> SEQUENCE: 40

Pro Gln Gln Leu His Ala Ser Glu Val Leu Ser Ser Gly Phe Arg Leu
 1               5                  10                  15

Ser Trp Pro Pro Leu Leu Thr Ala Asp Ser Gly Tyr Tyr Val Leu Glu
                20                  25                  30

Leu Val Pro Ser Gly Lys Leu Ala Thr Thr Arg Arg Gln Gln Leu Pro
            35                  40                  45

Gly Asn Ala Thr Ser Trp Thr Trp Thr Asp Leu Asp Pro Asp Thr Asp
 50                  55                  60

Tyr Glu Val Ser Leu Leu Pro Glu Ser Asn Val His Leu Leu Arg Pro
65                   70                  75                  80

Gln His Val Arg Val Arg Thr
                85
```